United States Patent
Ori et al.

(10) Patent No.: US 8,362,105 B2
(45) Date of Patent: Jan. 29, 2013

(54) DENTAL CURABLE COMPOSITION AND KIT FOR SUCH DENTAL CURABLE COMPOSITION

(75) Inventors: Tatsuya Ori, Moriyama (JP); Haruka Nishitani, Moriyama (JP); Yuya Yamamoto, Moriyama (JP); Takashi Yamamoto, Moriyama (JP)

(73) Assignee: Sun Medical Co., Ltd., Moriyama-shi (JP)

( * ) Notice: Subject to any disclaimer, the term of this patent is extended or adjusted under 35 U.S.C. 154(b) by 347 days.

(21) Appl. No.: 12/063,200

(22) PCT Filed: Aug. 8, 2006

(86) PCT No.: PCT/JP2006/315685
§ 371 (c)(1),
(2), (4) Date: Feb. 7, 2008

(87) PCT Pub. No.: WO2007/018220
PCT Pub. Date: Feb. 15, 2007

(65) Prior Publication Data
US 2009/0137697 A1    May 28, 2009

(30) Foreign Application Priority Data
Aug. 8, 2005   (JP) ................................ 2005-229625

(51) Int. Cl.
*A61K 6/08* (2006.01)
*A61F 2/00* (2006.01)
(52) U.S. Cl. ........................................ 523/116; 523/115
(58) Field of Classification Search .................... 523/116
See application file for complete search history.

(56) References Cited

U.S. PATENT DOCUMENTS

| 1,030,598 | A | | 1/1989 | Sakashita et al. |
| 4,920,188 | A | | 4/1990 | Sakashita et al. |
| 5,063,257 | A | | 11/1991 | Akahane et al. |
| 5,228,907 | A | * | 7/1993 | Eppinger et al. ................ 106/35 |
| 5,520,725 | A | | 5/1996 | Kato et al. |
| 6,071,983 | A | * | 6/2000 | Yamamoto et al. ........... 523/118 |
| 6,288,138 | B1 | * | 9/2001 | Yamamoto et al. ........... 523/118 |
| 6,291,548 | B1 | | 9/2001 | Akahane et al. |
| 7,351,753 | B2 | | 4/2008 | Qian |
| 2005/0070627 | A1 | * | 3/2005 | Falsafi et al. .................. 523/115 |

FOREIGN PATENT DOCUMENTS

| JP | 2164807 A | 6/1990 |
| JP | 6009327 A | 1/1994 |
| JP | 7097306 A | 4/1995 |
| JP | 7291819 A | 11/1995 |
| JP | 8026925 A | 1/1996 |
| JP | 2000053518 A | 2/2000 |
| JP | 2000178111 A | 6/2000 |
| JP | 2003238325 A | 8/2003 |
| JP | 2004189661 A | 7/2004 |
| JP | 2005008622 A | 1/2005 |

* cited by examiner

*Primary Examiner* — Peter F Godenschwager
*Assistant Examiner* — David Karst
(74) *Attorney, Agent, or Firm* — The Webb Law Firm

(57) ABSTRACT

A dental curable composition has a curing time of 30 seconds to 120 minutes and includes a compound having an acidic group in the molecule (A), a polymerizable monomer (B), an organic amine compound (C) and a sulfur-containing reducing compound (D). In the dental curable composition, the content of the component (A) is 0.01 to 80 parts by weight, the content of the component (B) is 21 to 99.8 parts by weight, the content of the component (C) is 0.01 to 30 parts by weight and the content of the component (D) is 0 to 30 parts by weight. The composition may be cured at a relatively low temperature close to the body temperature without using a peroxide-based polymerization initiator, and has good sealing properties and adhesion.

20 Claims, No Drawings

DENTAL CURABLE COMPOSITION AND KIT FOR SUCH DENTAL CURABLE COMPOSITION

TECHNICAL FIELD

The present invention relates to a dental curable composition which can bond to teeth and is usable as a bonding material, a cement, a root canal filling material, other filling materials for repairing a tooth cavity, and the like. More particularly, the present invention relates to a dental curable composition which is composed of a liquid material and a powder material or is a combination of two or more paste compositions which are mixed when used, the composition having excellent polymerizability and bond durability without requiring a tooth surface treatment or a primer treatment and containing no peroxides; and relates to a kit for the dental curable composition.

BACKGROUND ART

Methods of repairing cavities caused by caries and the like include generally the following methods.

The first one is a repairing treatment method using a prosthesis such as a crown or inlay with a material called a luting cement, and the second one is a repairing treatment method using a filling material such as a composite resin with an adhesive resin.

Representative luting cements used today in the above method include a glass ionomer cement, a resin-reinforced glass ionomer cement and a resin cement. It is explained that the glass ionomer cement may bond to tooth substance by chelate bond and that the sustained-release of fluorine from the cement inhibits the progress of caries by helping the recalcification of tooth substance and by inhibiting the sugar metabolism and acid production by *Streptococcus mutans*. However, any conclusive evidence of the adhesion is not yet provided and there is no clear presentation on the effective concentration and sustained-release period of fluorine which may contribute to the recalcification. In addition, the glass ionomer cement has problems that the physical properties of the cement per se are deteriorated when the cement is contacted with moisture such as saliva at the early stage of curing, and above all, the cement is decomposed under wet and acidic conditions usually encountered in the oral cavity, causing secondary caries.

With the above problems, there have been disclosed various resin-reinforced glass ionomer cements for which the issue of water-sensitive properties is especially considered (Patent Documents 1, 2 and 3). These are compositions made by blending a glass ionomer cement component with a monomer having a polymerizable ethylenically unsaturated double bond and a polymerization catalyst. It is considered that the decomposition of the cement under the conditions in the oral cavity is reduced by the addition and polymerization of the resin component (polymerizable monomer and polymerization catalyst). However, a fundamental solution is not achieved.

On the other hand, it is accepted that the resin cement does not have water-sensitive properties unlike the glass ionomer cement and is excellent in tooth substance adhesion. However, stable tooth substance adhesion is not obtained unless the teeth are treated by surface treatment, primer treatment or the like with an acidic aqueous solution such as phosphoric acid. Especially, a cut dentin surface is frequently wet with an exudate and the like and therefore the pretreatment before the bonding is complicated. It may be considered that the resin cement is a technique-sensitive material and requires skills in handling.

Commercially available resin cements are divided into two types: one is a chemically polymerizable resin using a redox initiator composed of a peroxide and an amine compound, and the other is a dual-cure resin in which the redox initiator is combined with a photo-polymerization initiator. Both types have chemical polymerizability in case they are applied to area where light will not reach, for example in case they are used to bond an inlay, a crown and the like and to build an abutment. For this reason, there are problems that they are susceptible to polymerization inhibition by water, oxygen and the like under an oral cavity environment and the polymerizability is reduced at the bonding interface due to the exudates especially when the resin cements are applied to the dentin surface. Such problems often cause secondary caries. In addition, the polymerization heat generated at the time of polymerization is unpleasant for patients, and the resin derived from the amine compound is discolored with time.

Further, as the second repairing treatment method, there has been proposed a dental adhesive composition and a kit for repairing cavities using an adhesive resin (Patent Document 4). This composition is composed of a polymerizable monomer, a polymerization initiator, a reducing agent and water. However, camphorquinone is essential as a polymerization initiator in order to ensure sufficient bonding performance and durability to teeth, and further at least a given amount (0.01% by weight) of camphorquinone based on the composition is required.

[Patent Document 1] Japanese Patent Application Publication No. H6-27047

[Patent Document 2] Japanese Patent Laid-Open Publication No. H8-26925

[Patent Document 3] Japanese Patent Laid-Open Publication No. 2000-53518

[Patent Document 4] Japanese Patent Laid-Open Publication No. 2003-238325

Problems to be Solved by the Invention

An object of the present invention is to provide a dental curable composition that is not susceptible to polymerization inhibition due to water under wet conditions, generates small polymerization heat, has excellent adhesion to teeth without surface treatment, causes no gaps in the bonding interface, and has excellent decomposition resistance and no injurious effect on the dental pulp.

SUMMARY OF THE INVENTION

In view of the problems described above and as a result of the earnest studies to achieve the above object, the present inventors have found that a composition that is not susceptible to polymerization inhibition even under wet conditions in the substantial absence of a peroxide and the like and generates polymerization heat nearly equal to the body temperature has excellent adhesion to teeth without surface treatment, causes no gaps in the bonding interface, and has excellent decomposition resistance and no injurious effect on the dental pulp. The inventors have accomplished the present invention based on the finding.

A dental curable composition of the present invention has a curing time of 30 seconds to 120 minutes and comprises:

(A) a compound having an acidic group in the molecule, (B) a polymerizable monomer, (C) an organic amine compound, and (D) a sulfur-containing reducing compound; and contains in the dental curable composition, the component (A) in an amount of 0.01 to 80 parts by weight, the component (B) in an amount of 21 to 99.8 parts by weight, the component (C) in an amount of 0.01 to 30 parts by weight, and the component (D) in an amount of 0 to 30 parts by weight (wherein the total of the components (A) to (D) is 100 parts by weight; and when any compound belongs to a plurality of the components (A) to (D), the parts by weight of the compound is divided by the number of the components to which the compound belongs, and the quotient is used as the content of each component).

In the present invention, when any compound belongs to two or more of the components (A) to (D), the weight of the compound is divided by the number of the components to which the compound belongs, and the quotient is considered to express the amount of each component. For example, when a compound X has an acidic group and a polymerizable group in the molecule, the compound X is a compound (A) having an acidic group in the molecule and also is a polymerizable monomer (B) in the dental curable composition of the present invention. When the dental curable composition of the present invention contains x parts by weight of the compound X, x/2 parts by weight is the amount of the component (A) and x/2 parts by weight is the amount of the component (b) The total amount of the components (A) to (C) contained in the dental curable composition of the present invention is 100 parts by weight.

The dental curable composition (first dental curable composition) of the present invention has the above constitution and may further contain a component (X) which does not belong to any of the components (A) to (D). Further, a second dental curable composition of the present invention contains an aqueous solvent (E) in addition to the above components (A) to (D). A third dental curable composition of the present invention further contains a filling material (F). A fourth dental curable composition of the present invention further contains a small amount of a photo-polymerization initiator (G).

Meanwhile, when the dental curable composition of the present invention is used as a root canal filling material, especially a sealer cement for root canal obturation, there may be provided a sealer cement for root canal obturation in which polymerization occurs from the tooth substance interface irrespective of the wet conditions in the root canal and which has excellent tooth substance adhesion and marginal sealing properties.

Since no peroxide is blended as a polymerization initiator to the dental curable composition of the present invention, the polymerization is not inhibited even under wet conditions and the polymerization heat generated at the time of the reaction is nearly equal to the body temperature. Further, the dental curable composition of the present invention has excellent adhesion to teeth which are not subjected to surface treatment, and causes no gaps in the bonding interface; and a cured product of the composition is excellent in decomposition resistance and does not injure the dental pulp.

DETAILED DESCRIPTION OF THE INVENTION

The dental curable composition of the present invention has a curing time of 30 seconds to 120 minutes, preferably 2 to 60 minutes and more preferably 5 to 35 minutes. When the curing time is less than the lower limit of the above range, the composition is cured during kneading and may not be used. When the curing time exceeds the upper limit of the above range, the polymerization will be inhibited by the exudates. The term "curing time" means a time from the start of polymerization to the curing, and the polymerization is typically induced by light application with a light irradiator for polymerization, by mixing a polymerization initiator, or the like. In addition, the term "curing" means the completion of a polymerization run. The progress of the curing reaction may be grasped, for example, by determining the calorific value generated by polymerization reaction over time using a differential scanning calorimeter.

Further, the polymerization temperature at which the dental curable composition of the present invention is polymerized is preferably 60° C. or lower, more preferably 50° C. or lower and further more preferably 45° C. or lower. When the polymerization temperature is higher than the above temperature, the patient feels pain or discomfort. Meanwhile, the polymerization temperature may be determined with a differential scanning calorimeter.

The dental curable composition of the present invention contains a compound having an acidic group in the molecule (A), a polymerizable monomer (B), and an organic amine compound (C); and usually contains a sulfur-containing reducing compound (D). A peroxide-based polymerization initiator is not substantially contained in the dental curable composition. In the present invention, that a peroxide-based polymerization initiator is not substantially contained means not only that any peroxide-based polymerization initiator is not at all contained but also that the dental curable composition contains a peroxide-based polymerization initiator in an amount of 0.01 part by weight or less or 0.001 part by weight or less when the total amount of the dental curable composition is 100 parts by weight. Conventionally, the peroxide-based polymerization initiators are essential in the practical dental curable compositions of similar type in order to cure the compositions. However, because of the combination of the components in the invention, the dental curable composition of the invention does not substantially contain a peroxide-based polymerization initiator as an essential component. The dental curable composition of the present invention does not contain a peroxide-based polymerization initiator and has a curing time controlled to 30 seconds to 120 minutes. In particular, this curing time is appropriate for the composition to be used extremely easily as a sealer.

The dental curable composition of the present invention, as mentioned above, contains a compound having an acidic group in the molecule (A).

In the present invention, the compound having an acidic group in the molecule (A) may be a compound having an acidic group or may be a compound which does not have an acidic group in the apparent structure but is easily converted to a compound having an acidic group in an aqueous solvent system at a temperature close to room temperature (for example, an acid anhydride and the like).

The compounds having an acidic group in the molecule (A) include, for example, compounds having an acidic group in the molecule but having no polymerizability ($A_0$) polymerizable monomers having an acidic group and a polymerizable group in the molecule (AB), and the like.

As the compounds having an acidic group in the molecule but having no polymerizability ($A_0$) used as the compounds having an acidic group in the molecule (A) in the present invention, there may be mentioned, for example, inorganic acids and organic acids having no polymerizable groups.

The inorganic acids which may be used as ($A_0$) in the present invention include, for example, carbonic acid, phosphoric acid and the like.

In addition, as the organic acids having no polymerizable groups which may be used as ($A_0$) in the present invention, there may be mentioned, for example, monobasic acids such as formic acid, acetic acid and propionic acid; dibasic acids such as oxalic acid, succinic acid and adipic acid; hydroxycarboxylic acids such as lactic acid, glycolic acid, tartaric acid, malic acid, citric acid, ascorbic acid, gluconic acid and glyceric acid; acidic amino acids such as glutamic acid and aspartic acid, keto acids such as pyruvic acid, acetoacetic acid and levulinic acid, aromatic carboxylic acids such as benzoic acid and salicylic acid, and polycarboxylic acids such as ethylenediamine tetraacetic acid; and others such as isocitric acid, malonic acid, glutaric acid, glucuronic acid, kojic acid, phytic acid, aconitic acid, and glycerophosphoric acid. The components ($A_0$) may be used alone or in combination with one another. In addition, acid anhydrides of these acids may be used alone or in combination in the present invention.

In the dental curable composition of the present invention, the polymerizable monomer (B) is not particularly limited as long as it is a monomer which is polymerized by a radical polymerization initiator. Examples thereof include, for example, radical-polymerizable monomers having polymerizable groups such as a (meth)acryloyl group, styryl group, vinyl group, allyl group and the like.

The polymerizable monomer (B) used in the present invention contains at least one group selected from the above polymerizable groups in the molecule.

In the present invention, examples of the polymerizable monomers (B) include monofunctional polymerizable monomers having one group of the above polymerizable groups in the molecule, and difunctional or tri- or poly-functional polymerizable monomers having two or three or more polymerizable groups. These monomers may be selected and used appropriately depending on the intended use and the like.

As the polymerizable monomers (B) in the present invention, there may be used polymerizable monomers which have no acidic group in the molecule ($B_0$), polymerizable monomers which have an acidic group in the molecule (AB), and the like.

First, there will be explained the polymerizable monomers having no acidic group in the molecule ($B_0$) which are the polymerizable monomers (B).

The polymerizable monomers having no acidic group in the molecule ($B_0$) include monofunctional polymerizable monomers (i), difunctional polymerizable monomers (ii) and polyfunctional polymerizable monomers (iii). Among these, the monofunctional polymerizable monomers (i) include, for example, linear or branched alkyl(meth)acrylates such as methyl (meth)acrylate, ethyl(meth)acrylate, propyl(meth)acrylate, isopropyl(meth)acrylate, butyl(meth)acrylate, pentyl(meth)acrylate and isopentyl(meth)acrylate;

heterocyclic (meth)acrylates containing an oxygen atom and the like such as glycidyl(meth)acrylate and tetrahydrofurfuryl(meth)acrylate;

hydroxyalkyl(meth)acrylates such as 2-hydroxyethyl (meth)acrylate and 2-hydroxypropyl(meth)acrylate;

the above hydroxyalkyl (meth)acrylates further containing a halogen such as chlorine, for example, 3-chloro-2-hydroxypropyl(meth)acrylate and the like;

alkoxypolyethylene glycol (meth)acrylates such as ethylene glycol mono(meth)acrylate, diethylene glycol mono (meth)acrylate, triethylene glycol mono(meth)acrylate, polyethylene glycol mono(meth)acrylate, methoxydiethylene glycol mono(meth)acrylate, methoxytetraethylene glycol (meth)acrylate, and methoxypolyethylene glycol (meth)acrylate; and the like.

The difunctional polymerizable monomers (ii) include, for example, linear or branched, poly- or mono-alkylene glycol di(meth) acrylates such as methylene glycol di(meth)acrylate, ethylene glycol di(meth)acrylate, diethylene glycol di(meth)acrylate, triethylene glycol di(meth)acrylate, propylene glycol di(meth)acrylate, tetraethylene glycol di(meth)acrylate, polyethylene glycol di(meth)acrylate, 1,3-butyleneglycol di(meth)acrylate and neopentylglycol di(meth)acrylate.

The polyfunctional polymerizable monomers (iii) include, for example, trifunctional polymerizable monomers such as trimethylolalkane tri(meth)acrylates including trimethylolmethane tri (meth)acrylate, trimethylolethane tri(meth)acrylate and trimethylolpropane tri(meth)acrylate, and (meth)acrylate esters of tris(2-hydroxyethyl)isocyanurate;

tetrafunctional polymerizable monomers such as tetra (meth)acrylates of polymethylolalkanes or ethers thereof such as pentaerythritol tetra(meth)acrylate, pentaerythritol tetra(meth)acrylate and ditrimethylolpropane tetra(meth) acrylate (O(—CH$_2$—C(—CH$_2$O—CO—CR═CH$_2$)$_2$CH$_2$CH$_3$)$_2$, R: H or CH$_3$); and penta- or more functional polymerizable monomers such as poly(meth)acrylates of polymethylolalkanes or ethers thereof such as dipentaerythritol hexa(meth)acrylate and dipentaerythritol hydroxypenta(meth)acrylate.

Examples of the di- or poly-functional polymerizable monomers further include compounds which have a methacrylate group and an acrylate group in the molecule such as, for example, triethylene glycol acrylate methacrylate, trimethylolpropane monoacrylate dimethacrylate and pentaerythritol diacrylate dimethacrylate.

Of the polymerizable monomers (B), especially preferred are the polymerizable monomers containing a hydroxyl group and the polymerizable monomers containing a triazine ring in the molecule (isocyanurate (meth)acrylate esters and the like). The polymerizable monomers may be used alone or in combination.

The polymerizable monomers containing a hydroxyl group in the molecule may further contain other functional groups such as a hydroxyl group, an amino group and a glycidyl group in the molecule.

For example, in the case of monomers having a (meth) acryloyl group, examples of the hydroxy monomers with other functional groups include:

(meth)acrylates containing a hydroxyl group such as 2-hydroxyethyl(meth)acrylate, 2- or 3-hydroxypropyl(meth)acrylate, 4-hydroxybutyl(meth)acrylate, 5-hydroxypentyl(meth) acrylate, 6-hydroxyhexyl(meth)acrylate, 10-hydroxydecyl (meth)acrylate, 1,2- or 1,3- and 2,3-dihydroxypropane(meth) acrylate, diethylene glycol mono(meth)acrylate, triethylene glycol mono(meth)acrylate, pentaethylene glycol mono (meth)acrylate, polyethylene glycol mono(meth)acrylate and dipropylene glycol mono(meth)acrylate;

(meth)acrylamides containing a hydroxyl group such as methylol(meth)acrylamide, N-(meth)acryloyl-2,3-dihydroxypropylamine and N-(meth)acryloyl-1,3-dihydroxypropylamine; and addition products of GMA and aliphatic or aromatic polyols (including phenols) such as 2-hydroxy-3-phenoxypropyl (meth)acrylate (HPPM in the case of methacrylate), 2-hydroxy-3-naphthoxypropyl(meth)acrylate (HNPM in the case of methacrylate), and an addition reaction product of 1 mol of bisphenol A and 2 mol of glycidyl (meth)acrylate (GMA in the case of methacrylate) (Bis-GMA in the case of methacrylate).

As mentioned above, the dental curable composition of the present invention may contain a compound which belongs to both "the compound having an acidic group in the molecule (A)" and "the polymerizable monomer (B)". In the present invention, such compound belonging to both the component (A) and the component (B) is referred to as the component (AB). The component (AB) is a polymerizable monomer having an acidic group and a polymerizable group in the molecule. In the present invention, a functional group which may be readily converted to an acidic group will be considered as an acidic group. An acid anhydride is an example of such functional groups. As the acidic groups contained in the component (AB) as mentioned above, there may be mentioned, for example, a carboxylic acid group, a phosphoric acid group, a pyrophosphoric acid group, a thiophosphoric acid group, a sulfonic acid group, a sulfinic acid group and acid anhydrides of these acids. The component (AB) preferably contains at least one of these acidic groups.

Of the polymerizable monomers which may be used as the component (AB), the polymerizable monomers having at least one carboxyl group in the molecule include monocarboxylic acids, dicarboxylic acids, tricarboxylic acids, tetracarboxylic acids and derivatives of these acids. Examples include:

compounds in which a carboxyl group is directly bonded to the vinyl group, such as (meth)acrylic acid, fumaric acid, maleic acid and the like;

compounds in which an aromatic ring is directly bonded to the vinyl group, such as p-vinylbenzoic acid and the like;

compounds having a (meth)acryloyloxy group such as 11-(meth)acryloyloxy-1,1-undecanedicarboxylic acid (MAC-10 in the case of methacrylate);

aromatic carboxylic acid compounds having a (meth)acryloyloxyalkyl group such as 1,4-di(meth)acryloyloxyethyl pyromellitic acid and 6-(meth)acryloyloxyethylnaphthalene-1,2,6-tricarboxylic acid;

(hydroxy)(meth)acryloyloxyalkyltrimellitic acid compounds and anhydrides thereof such as 4-(meth)acryloyloxymethyltrimellitic acid and anhydride thereof, 4-(meth)acryloyloxyethyltrimellitic acid (4-MET in the case of methacrylate) and anhydride thereof (4-META in the case of methacrylate), 4-(meth)acryloyloxybutyltrimellitic acid and anhydride thereof, and 4-[2-hydroxy-3-(meth)acryloyloxy]butyltrimellitic acid and anhydride thereof;

compounds having a carboxybenzoyloxy group such as 2,3-bis(3,4-dicarboxybenzoyloxy)propyl(meth)acrylate and the like;

N- and/or O-(meth)acryloyloxy amino acids such as N,O-di(meth)acryloyloxy tyrosine, O-(meth)acryloyloxy tyrosine, N-(meth)acryloyloxy tyrosine and N-(meth)acryloyloxyphenyl alanine;

(meth)acryloylaminobenzoic acids such as N-(meth)acryloyl-p-aminobenzoic acid, N-(meth)acryloyl-O-aminobenzoic acid, N-(meth)acryloyl-5-aminosalicylic acid (5-MASA in the case of methacrylate) and N-(meth)acryloyl-4-aminosalicylic acid;

addition products such as addition products of 2-hydroxyethyl(meth)acrylate and pyromellitic dianhydride (PMDM in the case of methacrylate), addition products of 2-hydroxyethyl(meth)acrylate and maleic anhydride or 3,3',4,4'-benzophenonetetracarboxylic dianhydride (BTDA in the case of methacrylate) or 3,3',4,4'-biphenyltetracarboxylic dianhydride, and addition products of 2-(3,4-dicarboxybenzoyloxy)-1,3-di(meth)acryloyloxypropane, N-phenylglycine or N-tolylglycine with glycidyl(meth)acrylate;

compounds having an alcoholic hydroxyl group such as 4-[(2-hydroxy-3-(meth)acryloyloxypropyl)amino]phthalic acid and 3- or 4-[N-methyl-N-(2-hydroxy-3-(meth)acryloyloxypropyl)amino]phthalic acid; and the like. Among these, preferably used are MAC-10, 4-MET, 4-META and 5-MASA. These polymerizable monomers having the carboxyl group may be used alone or in combination. In the present specification, the term "(meth)acrylic acid" means both acrylic acid and methacrylic acid, and the same applies to the term "(meth)acrylate".

Of the polymerizable monomers which may be used as the component (AB), the polymerizable monomers having at least one phosphoric acid group in the molecule include:

(meth)acryloyloxyalkyl acid phosphate compounds such as 2-(meth)acryloyloxyethyl acid phosphate, 2- and 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate and 12-(meth)acryloyloxydodecyl acid phosphate;

bis[(meth)acryloyloxyalkyl]acid phosphates such as bis[2-(meth) acryloyloxyethyl]acid phosphate and bis[2- or 3-(meth)acryloyloxypropyl]acid phosphate;

(meth)acryloyloxyalkylphenyl acid phosphates having 0 or more substituents in the aromatic ring such as 2-(meth)acryloyloxyethylphenyl acid phosphate and 2-(meth) acryloyloxyethyl-p-methoxyphenyl acid phosphate; and the like. The phosphoric acid group in these compounds may be substituted by a thiophosphoric acid group. Among these, preferably used are 2-(meth)acryloyloxyethylphenyl acid phosphate and 10-(meth)acryloyloxydecyl acid phosphate. These polymerizable monomers having the phosphoric acid group may be used alone or in combination.

Of the polymerizable monomers which may be used as the component (AB), the polymerizable monomers having at least one pyrophosphoric acid group in the molecule include:

di[(meth)acryloyloxyalkyl]pyrophosphate compounds such as di[2-(meth)acryloyloxyethyl]pyrophosphate, di-4-(meth)acryloyloxybutyll pyrophosphate, di[6-(meth)acryloyloxyhexyl]pyrophosphate, di[8-(meth)acryloyloxyoctyl]pyrophosphate and di[10-(meth)acryloyloxydecyl]pyrophosphate; and the like.

These polymerizable monomers having the pyrophosphoric acid group may be used alone or in combination.

Of the polymerizable monomers which may be used as the component (AB), the polymerizable monomers having at least one sulfonic acid group in the molecule include:

sulfoalkyl(meth)acrylate compounds such as 2-sulfoethyl(meth)acrylate, 2- or 1-sulfo-1- or 2-propyl(meth)acrylate and 1- or 3-sulfo-2-butyl(meth)acrylate;

the above sulfoalkyl(meth)acrylate compounds further having a heteroatom or a substituent such as 3-bromo-2-sulfo-2-propyl(meth)acrylate and 3-methoxy-1-sulfo-2-propyl(meth)acrylate;

sulfoalkyl(meth)acrylamides having a substituent such as 1,1-dimethyl-2-sulfoethyl(meth)acrylamide; and the like. Among these, preferably used is 2-methyl-2-(meth)acrylamidopropane sulfonic acid. These polymerizable monomers having the sulfonic acid group may be used alone or in combination.

The above components (AB) may be used alone or in combination.

It is preferable that the compound having an acidic group in the molecule (A) has a larger acid strength, in other words, has a larger acid dissociation constant than the organic amine compound (C), irrespective of whether the compound is the compound having an acidic group in the molecule but having no polymerizability ($A_O$) or the polymerizable monomer having an acidic group and a polymerizable group in the molecule (AB).

In the dental curable composition of the present invention, examples of the organic amine compounds (C) include, for example, aromatic amines such as N,N-dimethylaniline, N,N-dimethyl-p-toluidine (DMPT), N,N-diethanol-p-toluidine (DEPT), N,N-dimethyl-p-tert-butylaniline, N,N-dimethylanisidine, N,N-dimethyl-p-chloroaniline, N,N-dimethylaminobenzoic acid and alkyl esters thereof, N,N-diethylaminobenzoic acid (DEABA) and alkyl esters thereof and N,N-dimethylamino benzaldehyde (DMABAd); N-phenylglycine (NPG), N-tolylglycine (NTG), N-(3-methacryloyloxy-2-hydroxypropyl)-N-phenylglycine (NPG-GMA), and the like.

In particular, in order to securely cure the dental curable composition of the present invention without using an organic peroxide and further improve the adhesion to the tooth substance, there is preferably used an organic amine compound represented by the following formula (I) which is an aromatic amine having a carbonyl group, or an organic amine compound represented by the following formula (II) which is an aromatic amine having a carbonyl group. Among these, the organic amine compound represented by the following formula (I) is preferable because it functions also as a photoinitiator.

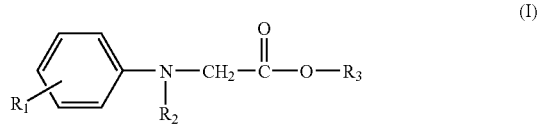

(I)

In the formula (I), $R_1$ and $R_2$ are each independently a hydrogen atom or an alkyl group which may have a functional group or a substituent, and $R_3$ is a hydrogen atom or a metal atom.

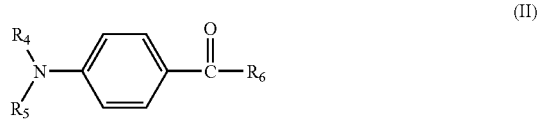

(II)

In the formula (II), $R_4$ and $R_5$ are each independently a hydrogen atom or an alkyl group, and $R_6$ is a hydrogen atom or an alkyl group or an alkoxyl group which may have a functional group or a substituent.

The organic amine compounds represented by the above formula (I) include, for example, NPG, NTG, NPG-GMA and the like already described. Among these, NPG is preferably used; however, since a salt thereof (alkali metal salt or alkali earth metal salt) is unlikely to cause discoloration during the storage at room temperature and is excellent in color tone stability, N-phenylglycine potassium salt and N-phenylglycine sodium salt are especially preferably used.

In addition, when NPG and the like are used among the organic amine compounds (C), NPG and the like preferably have low content of impurities. More specifically, the impurities are various impurities generated when NPG not forming a salt is allowed to stand at room temperature in the air. Since the impurities are likely to impair the effect of the present invention, it is preferable that the impurity generation is prevented and the impurities are removed with good accuracy. In other words, the content of impurities is preferably not more than 10% by weight, more preferably not more than 5% by weight and further more preferably not more than 1% by weight, relative to 100% by weight of NPG or an analogous compound.

Further, the organic amine compounds represented by the formula (II) include aliphatic alkylaminobenzoic acids and alkyl esters thereof such as the already described N,N-dimethylaminobenzoic acid and alkyl esters thereof, N,N-diethylaminobenzoic acid (DEABA) and alkyl esters thereof, and N,N-dipropylaminobenzoic acid and alkyl esters thereof, N-isopropylaminobenzoic acid and alkyl esters thereof, N-isopropyl-N-methylaminobenzoic acid and alkyl esters thereof; aliphatic alkylaminobenzaldehydes such as DMABAd, N,N-diethylaminobenzaldehyde, N,N-dipropylaminobenzaldehyde, N-isopropyl-N-methylaminobenzaldehyde and the like; aliphatic alkylaminoacetylbenzenes such as N,N-dimethylaminoacetylbenzene, N,N-diethylaminoacetylbenzene, N,N-dipropylaminoacetylbenzene, N-isopropylaminoacetylbenzene, N-isopropyl-N-methylaminoacetylbenzene and the like; and aliphatic alkylaminoacylbenzenes. These organic amine compounds may be used alone or in combination.

Some of the organic amine compounds used in the present invention, for example NPG (N-phenylglycine), contain an amino group and a carboxyl group. The compounds containing an amino group and a carboxyl group are also referred to as the components (CA). For example, when the component (CA) is contained in an amount of z parts by weight in the dental curable composition of the present invention, z/2 parts by weight is the amount of the component (A) and z/2 parts by weight is the amount of the component (C).

In the dental curable composition of the present invention, the sulfur-containing reducing compound (D) is not particularly limited as long as higher reducing properties are obtained with the increase of the oxidation number of the sulfur atom. Examples thereof include organic sulfur-containing compounds and inorganic sulfur-containing compounds. The sulfur-containing reducing compounds may be used alone or in combination of two or more kinds of them. As the organic sulfur-containing compound, for example, preferable is an organic sulfur-containing compound in which the sulfur-containing reducing compound is selected from the group consisting of an organic sulfinic acid, an organic sulfinic acid salt, an organic sulfonic acid and an organic sulfonic acid salt. Specific examples of the organic sulfur-containing compounds include aromatic sulfinic acids and salts thereof such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid; aromatic sulfonic acids and salts thereof such as benzenesulfonic acid, o-toluenesulfonic acid, p-toluenesulfonic acid, ethylbenzenesulfonic acid, decylbenzenesulfonic acid, dodecylbenzenesulfonic acid, chlorobenzenesulfonic acid and naphthalenesulfonic acid; and the like. Among these, p-toluenesulfinate salt is preferably used and especially sodium p-toluenesulfinate is preferably used.

The inorganic sulfur-containing compounds include, for example, sulfurous acid, bisulfurous acid, metasulfurous acid, metabisulfurous acid, pyrosulfurous acid, thiosulfuric acid, 1,2-dithionous acid, 1,2-thionic acid, hyposulfurous acid, hydrosulfurous acid and salts thereof. Among these, a sulfurous acid salt is preferably used, and especially sodium sulfite, potassium sulfite, sodium bisulfite and potassium bisulfite are preferably used. These organic and inorganic sulfur-containing compounds may be used alone or in combination.

The first dental curable composition of the present invention preferably contains 0.01 to 80 parts by weight of the component (A), 21 to 99.8 parts by weight of the component (B), 0.01 to 30 parts by weight of the component (C) and 0 to 30 parts by weight of the component (D) (the total amount of the components (A) to (D) is 100 parts by weight). More preferably, the first dental curable composition contains 3.05 to 70 parts by weight of the component (A), 33 to 95 parts by weight of the component (B), 0.01 to 20 parts by weight of the component (C) and 0.02 to 20 parts by weight of the component (D) (the total amount of the components (A) to (D) is 100 parts by weight). Further more preferably, the first dental curable composition contains 5.1 to 60 parts by weight of the component (A), 45 to 90 parts by weight of the component (B), 0.03 to 15 parts by weight of the component (C) and 0.02 to 15 parts by weight of the component (D) (the total amount of the components (A) to (D) is 100 parts by weight). Especially preferably, the first dental curable composition contains 7 to 50 parts by weight of the component (A), 50 to 85 parts by weight of the component (B) 0.05 to 15 parts by weight of the component (C) and 0.03 to 14 parts by weight of the component (D) (the total amount of the components (A) to (D) is 100 parts by weight).

In more detail, when the composition does not substantially contain the polymerizable monomer having an acidic group in the molecule (AB), the content of the nonpolymerizable compound having an acidic group in the molecule ($A_0$) which belongs to the component (A) is preferably 0.01 to 30 parts by weight, more preferably 0.05 to 25 parts by weight and further more preferably 0.10 to 20 parts by weight. When the content of the compound ($A_0$) is less than the lower limit of the above range, the decalcification of the tooth surface to which the composition is applied is insufficient. When the content of the compound ($A_0$) exceeds the upper limit, the excessive decalcification of the tooth surface and the leakage of the component ($A_0$) from the cured product after polymerization are likely to increase. On the other hand, the content of the polymerizable monomer having no acidic group in the molecule ($B_0$) which belongs to the component (B) is preferably 20 to 99.8 parts by weight, more preferably 30 to 95 parts by weight and further more preferably 40 to 90 parts by weight. When the content of the monomer ($B_0$) is less than the lower limit of the above range, the water resistance and physical properties of the cured product are likely to deteriorate. When the content of the monomer ($B_0$) exceeds the upper limit, the conformity with the tooth substance is likely to decrease. In particular, when the composition does not substantially contain the compound having an acidic group in the molecule ($A_0$), the content of the polymerizable monomer having an acidic group in the molecule (AB) is preferably 1 to 50 parts by weight, more preferably 3 to 45 parts by weight and further more preferably 5 to 40 parts by weight. When the content of the polymerizable monomer (AB) is less than the lower limit of the above range, the decalcification of the tooth surface to which the composition is applied and the diffusion of the polymerizable monomer to the tooth substance may be insufficient. When the content of the polymerizable monomer (AB) exceeds the upper limit, the decalcification of the tooth surface may be excessive.

Further, the weight ratio of $[(A_0)+(AB)]$ to ($B_0$) is preferably in the range of 60:40 to 0.1:99.9, more preferably 50:50 to 1:99, and further more preferably 40:60 to 10:90. When the weight ratio is less than the lower limit of the above range, the decalcification of the tooth surface to which the composition is applied and the diffusion of the polymerizable monomer to the tooth substance are insufficient. When the weight ratio exceeds the upper limit, the decalcification of the tooth surface is excessive. In addition, the weight ratio of ($A_0$) to $[(B_0)+(AB)]$ is preferably in the range of 15:85 to 0:100, more preferably 10:90 to 0:100, and further more preferably 5:95 to 0:100. When the weight ratio exceeds the upper limit of the above range, the excessive decalcification of the tooth surface and the leakage of the component ($A_0$) from the cured product after polymerization increase.

The ratio of the components may be determined based on the parts by weight of the components. Thus, the ratio (B/C) of the component (B) to the component (C) is 0.7 to 9980, preferably 3 to 3000 and more preferably 3 to 100.

Further, in the above components (A) to (D) and the like, there may be a material that belongs to two or more of the components.

The first dental curable composition may have a component (X) which does not belong to any of the components (A) to (D), and the content of the component (X) is preferably 0 to 80 parts by weight, more preferably 5 to 75 parts by weight and further more preferably 10 to 70 parts by weight when the total amount of the components (A) to (D) is 100 parts by weight. Representative examples of the component (X) include components (E) to (G) which are explained below.

The second dental curable composition of the present invention contains an aqueous solvent (E) in addition to the above components (A), (B), (C) and (D). The aqueous solvent (E) used here is water alone or a solvent in which water and an organic solvent miscible with water are mixed. Examples of water used here include, for example, distilled water and ion-exchanged water. In addition, saline may be used as an aqueous solvent. Among these, distilled water and ion-exchanged water are preferably used. Further, the organic solvents miscible with water include, for example, alcohols such as methanol, ethanol and propanol, ketones such as acetone and methylethylketone, ethers such as tetrahydrofuran, amides such as N,N-dimethylformamide, and the like. Among these, ethanol and acetone are especially preferably used, in consideration of the injurious effect and stimulation to the dental pulp.

In the second dental curable composition of the present invention containing the above components (A), (B), (C), (D) and (E), the content of the component (E) is preferably 0.1 to 70 parts by weight, more preferably 0.5 to 45 parts by weight and further more preferably 1 to 20 parts by weight (in 100 parts by weight of the composition in which the amount of any compound used as a plurality of the components is divided into respective amounts of the components). The relative ratio of the components (A) to (D) should be understood to be the same as in the first dental curable composition. When the ratio of the component (E) is high, the composition tends to show high primer properties and such composition may be practically used as a primer.

The third dental curable composition of the present invention contains the above components (A) to (D), a filling material (F) and optionally the component (E). The filling material (F) used in the present invention is at least one selected from inorganic filling materials, organic filling materials and organic composite filling materials. The shape of the filling material used in the present invention may be either spherical or amorphous. The shape and the particle size are determined appropriately.

As the inorganic filling material contained as the component (F) in the composition of the present invention, known sorts of filling materials may be used. For example, there may be mentioned metals of Groups I, II, III and IV of the Periodic Table and transition metals and oxides, hydroxides, chlorides, sulfates, sulfites, carbonates, phosphates and silicates thereof, and mixtures and composite salts thereof, and the like. More specifically, there may be mentioned silicon dioxide, glass powders of strontium glass, lanthanum glass, barium glass and the like, quartz powder, barium sulfate, aluminum oxide, titanium oxide, barium salts, glass beads, glass fibers, barium fluoride, lead salts, glass filling materials containing talc, colloidal silica, silica gel, zirconium oxide, tin oxide, carbon fibers, other ceramic powders, and the like. The inorganic filling material may be used as it is, but is preferably hydrophobized in order to increase the affinity between the inorganic filling material and the compound having an acidic group in the molecule (A) and the polymerizable monomer (B) and thereby to increase the blending amount of the inorganic filling material in the cement, or in order to prepare an organic composite filling material excellent in performance. The surface treating agent for hydrophobization may be a known agent with examples including silane coupling agents such as γ-(meth)acryloxypropyltrimethoxysilane, vinyltriethoxysilane, 3-aminopropylethoxysilane, 3-chloropropyltrimethoxysilane silylisocyanate, vinyltrichlorosilane, dialkyldichlorosilanes such as dimethyldichlorosilane and dioctyldichlorosilane, and hexamethylenedisilazane. Examples further include zirconium coupling agents and titanium coupling agents corresponding to the above coupling agents. As the surface treatment method, there are mentioned a method (dry method) in which the surface treating agent alone or the surface treating agent diluted with an aqueous organic solvent solution in which an organic solvent and water are uniformly mixed (such as an aqueous ethanol solution) is added to the inorganic filling material and mixed together with a ball mill, V-blender, Henschel mixer or the like, and then the resulting mixture is heat treated at 50 to 150° C. for several minutes to several hours; a method (wet method or slurry method) in which the inorganic filling material is added to an organic solvent such as ethanol, or a uniform solution of water with an organic solvent such as ethanol, or water to prepare a slurry and the surface treating agent is added to the slurry and the mixture is treated at from room temperature to a reflux temperature for several minutes to several hours, and then the solvent is removed by a known method such as decantation or evaporation followed by heat-treating the resulting product at 50 to 150° C. for several hours; and a method (spraying method) in which the surface treating agent or an aqueous solution thereof as described above is directly sprayed on the inorganic filling material at a high temperature. The inorganic filling material may be treated by an appropriate method in consideration of the properties of the silane treating agent and the inorganic filling material. Of course, a commercially available inorganic filling material which is already surface treated may be used as it is or may be further surface treated by the above methods and the like. Here, the above aqueous ethanol solution may be neutral or acidic. The amount of such surface treating agent used is preferably 0.1 to 60 parts by weight, especially preferably 0.1 to 45 parts by weight and most preferably 0.1 to 30 parts by weight, based on 100 parts by weight of the inorganic filling material.

In the present invention, examples of the organic filling materials used as the filling materials (F) include filling materials of polymer powder obtained by pulverization of a polymer or dispersion polymerization, and filling materials obtained by polymerizing a polymerizable monomer together with a crosslinking agent and pulverizing the resulting polymer. The polymerizable material which is used as a raw material for the filling material is not particularly limited. Preferable examples thereof include homopolymers and copolymers of the polymerizable monomers mentioned with respect to the component (B). For example, there may be mentioned poly(methylmethacrylate) (PMMA), poly(ethylmethacrylate), poly(propylmethacrylate), poly(butylmethacrylate) (PEBMA), polyvinyl acetate (PVAc), polyethylene glycol (PEG), polypropylene glycol (PPG), polyvinyl alcohol (PVA) and the like.

The organic composite filling materials include filling materials obtained by polymerization coating of the inorganic filling material surface with a polymerizable monomer followed by pulverization of the resulting material. Specifically, there may be mentioned pulverized products obtained by polymerization coating of fine powder silica, zirconium oxide or the like among the inorganic filling materials with the polymerizable monomer (A) or (B) followed by pulverization of the resulting material. As the organic composite filling material which is suitably used, there may be mentioned a filling material (TMPT.f) obtained by polymerization coating of the inorganic filling material with a polymerizable monomer based on trimethylolpropanetri(meth)acrylate (TMPT) followed by pulverization of the resulting material. These filling materials may be used alone or in combination.

In order to impart appropriate flowability to the dental curable composition, the average particle size of the filling material (F) is preferably 0.001 to 100 μm, more preferably 0.005 to 50 μm, further more preferably 0.01 to 20 μm and especially preferably 0.01 to 10 μm.

The third dental curable composition of the present invention contains the above components (A), (B), (C), (D) and the filling material (F), and further contains the component (E) as required. Here, the blending amount of the filling material (F) is 5 to 70 parts by weight and preferably 25 to 70 parts by weight in 100 parts by weight of the total of the above components (A), (B), (C), (D), (F) and the optional component (E).

Here, the relative ratio of the component (A), component (B), component (C), component (D) and component (E) should be understood to be the same as in the first and second dental curable compositions before the component (F) is added.

The fourth dental curable composition of the present invention includes the component (A), component (B), component (C), component (D) and a photo-polymerization initiator (G) (other than the photo-polymerization initiator represented by the formula (I)) and further includes the component (E) and the component (F) as required. The component (G) blended in the fourth composition of the present invention is a photo-polymerization initiator other than the photo-polymerization initiator represented by the formula (I). As the photo-polymerization initiator (G) which may be used in the present invention, there may be mentioned, for example, α-ketocarbonyl compounds, acylphosphineoxide compounds and the like. Specifically, the α-ketocarbonyl compounds include, for example, α-diketone, α-ketoaldehyde, α-ketocarboxylic acid, α-ketocarboxylic acid ester and the like.

In addition, as specific examples of the α-ketocarbonyl compounds, there may be mentioned α-diketones such as diacetyl, 2,3-pentadione, 2,3-hexadione, benzyl, 4,4'-dimethoxybenzyl, 4,4'-diethoxybenzyl, 4,4'-oxybenzyl, 4,4'-dichlorobenzyl, 4-nitrobenzyl, α-naphthyl, β-naphthyl, camphorquinone, camphorquinone sulfonic acid, camphorquinone carboxylic acid and 1,2-cyclohexanedione; α-ketoaldehydes such as methylglyoxal and phenylglyoxal; pyruvic acid, benzoylformic acid, phenylpyruvic acid, methyl pyruvate, ethyl benzoylformate, methyl phenylpyruvate, butyl phenylpyruvate and the like. Among these α-diketone carbonyl compounds, the α-diketones are preferably used in view of light stability. Among the α-diketones, diacetyl, benzyl and camphorquinone are preferably used.

In addition, as specific examples of the acylphosphineoxide compounds, there may be mentioned benzoyldimethoxyphosphine oxide, benzoylethoxyphenylphosphine oxide, benzoyldiphenylphosphine oxide, 2-methylbenzoyldiphenylphosphine oxide, 2,4,6-trimethylbenzoylphenylphosphine oxide and the like. These α-ketocarbonyl compounds and acylphosphine oxide compounds may be used alone or in combination. Especially in the present invention, camphorquinone and diphenyltrimethylbenzoylphosphine oxide are preferably used as the photo-polymerization initiator (G).

The fourth dental curable composition of the present invention includes the above components (A), (B), (C), (D) and the photo-polymerization initiator (G) (which is other than the photo-polymerization initiator represented by the formula (I)) and further includes the components (E) and (F) as required. The component (G) may be preferably contained in the range of 0.0001 to 5 parts by weight, more preferably 0.0002 to less than 0.01 part by weight and further more preferably in the range of 0.0005 to 0.005 part by weight in the fourth dental curable composition of the present invention. The relative ratio of the component (A), component (B), component (C), component (D), component (E) and the component (F) should be understood to be the same as in the first, second and third dental curable compositions.

The ratio of the components may be determined based on the parts by weight of the components. Thus, the ratio (G/C) of the component (G) to the component (C) is preferably 0.0000033 to 1050, more preferably 0.000007 to 0.05, further more preferably 0.000033 to less than 0.0005, and especially preferably 0.00007 to 0.0004.

The viscosity of the dental curable composition may be easily changed by using the component (F), and the components (A) to (F) may be mixed together in advance and the resultant composition may be applied to the tooth surface.

In an aspect of the present invention, a kit for a dental curable composition to obtain the above-mentioned dental curable composition is provided.

The dental curable composition of the present invention may change its form and performance during long storage, and the effect of the present invention may not be achieved. To solve such problems, the kit for a dental curable composition includes the aforementioned components that are separated and stored alone or in arbitrary combination. By mixing the components before use, the dental curable composition may be obtained. Needless to say, when all the components for the composition which are separated and stored are mixed in the total amounts (or dose by dose), the ratio of the amounts (parts by weight) of the components will be as described hereinabove. In the kit for a dental curable composition of the present invention, at least the compound having an acidic group in the molecule (A), and the organic amine compound (C) and/or the sulfur-containing reducing compound (D) are preferably placed separately from each other in containers A and C, respectively. Both the organic amine compound (C) and the sulfur-containing reducing compound (D) are more stable when they form salts with bases. However, in the presence of the compound having an acidic group in the molecule (A), the bases are substituted by protons and the compounds return to acids and are likely to be unstable. Therefore, they are preferably separated from each other. In this case, the polymerizable monomer having an acidic group in the molecule (AB) should be treated the same as the compound having an acidic group in the molecule (A).

It is also preferable that a small amount of the photo-polymerization initiator (G) is contained in the container A and/or the container C. Since the photo-polymerization initiator (G) is often poor in solubility, it is preferably pre-mixed in a liquid composition.

The polymerizable monomer having no acidic group in the molecule ($B_0$) is preferably contained in the container A and/or the container C. Because this polymerizable monomer is not acidic, the monomer does not cause problems when it is with the organic amine compound (C) and/or the sulfur-containing reducing compound (D).

It is preferable that the following relationship (1) is satisfied for the components placed in the containers A and C.

$$(b^A_a/B_a)+(b^C_c/B_c)=1$$

[$B_a$: 21/80 to 99.8/0.01 (preferably 33/70 to 95/3.05, more preferably 45/60 to 90/5.1)

$B_c$: 21/30 to 99.8/0.01 (preferably 33/20 to 95/0.01, more preferably 45/15 to 90/0.03)

$b^A_a$: The weight ratio (Polymerizable monomer(B)/Compound having an acidic group in the molecule (A)) in the composition placed in the container A $b^C_c$: The weight ratio (Polymerizable monomer(B)/Organic amine compound (C)) in the composition placed in the container C]

The above relation is preferably satisfied for the following reasons.

Assume that the composition in the container A includes $P^A_a$% by weight of the compound having an acidic group in the molecule (A) and $P^A_b$% by weight of the polymerizable monomer (B), and the composition in the container C includes $P^C_c$% by weight of the organic amine compound (C) and $P^C_b$% by weight of the polymerizable monomer (B). When the compositions are weighed and mixed together in an appropriate weight ratio (in amounts of $W^A$ and $W^C$ respectively), the resultant composition should contain the compound having an acidic group in the molecule (A), the polymerizable monomer (B) and the organic amine compound (C) in a suitable ratio to achieve the effect of the present invention. The ratio is specifically as follows:

$$B_a=(P^A_b*W^A+P^C_b*W^C)/(P^A_a*W^A)=P^A_b/P^A_a+(P^C_b*W^C)/(P^A_a*W^A) \quad (1)$$

$$B_c=(P^A_b*W^A+P^C_b*W^C)/(P^C_c*W^C)=(P^A_b*W^A)/(P^C_c*W^C)+P^C_b/P^C_c \quad (2),$$

wherein:

$B_a$=the polymerizable monomer (B)/the compound having an acidic group in the molecule (A)=21/(80-0.01)=21/79.99 to 99.8/0.01 (preferably 33/(70-0.01-0.02)=33/69.97 to 95/3.05, more preferably 45/(60-0.03-0.02)=45/59.95 to 90/5.1), and $B_c$=the polymerizable monomer (B)/the organic amine compound (C)=21/30 to 99.8/0.01 (preferably 33/20 to 95/0.01, more preferably 45/15 to 90/0.03).

When the equations (1) and (2) are transformed, $$B_a - P^A_b/P^A_a = (P^C_b*W^C)/(P^A_a*W^A) = (P^C_b/P^A_a)*(W^C/W^A) \quad (1')$$

$$B_c - P^C_b/P^C_c = (P^A_b*W^A)/(P^C_c*W^C) = (P^A_b/P^C_c)*(W^A/W^C) \quad (2')$$

Provided that (1')*(2')

$$\{B_a - P_b^A / P_a^A\} * \{B_c - P_b^C / P_c^C\} = (P_b^C / P_a^A) * (P_b^A / P_c^C) \quad (3)$$
$$= (P_b^A / P_a^A) * (P_b^C / P_c^C)$$

Above, ($P_b^A/P_a^A$) and ($P_b^C/P_c^C$) are the weight ratio (the polymerizable monomer (B)/the compound having an acidic group in the molecule (A)) in the composition in the container A and the weight ratio (the polymerizable monomer (B)/the organic amine compound (C)) in the composition in the container C, respectively. Therefore, when they are $b_a^A$ and $b_c^C$ respectively, (3) is:

$$(B_a - b_a^A) * (B_c - b_c^C) = b_a^A * b_c^C \quad (3')$$

When the equation (3') is further transformed for simplicity, $$B_a * B_c - B_a * b_c^C - B_c * b_a^A + b_a^A * b_c^C = b_a^A * b_c^C$$

$$B_a * B_c = B_a * b_c^C + B_c * b_a^A$$

$$(b_a^A / B_a) + (b_c^C / B_c) = 1 \quad (3'')$$

Here, $B_a$ is a composition ratio in the mixed product by which the effect of the present invention may be suitably developed, and $b_a^A$ is a composition ratio in the composition in the container C; therefore, they may not be equal.

This is the same in the case of $B_c$ and $b_c^C$ and they may not be equal.

In more detail, specific combinations are shown below.

In the container A is placed a liquid composition containing the component ($B_O$) and the component (AB), and optionally containing the component (E) and the component (G). In the container C is placed a powder composition containing the component (C) and the component (D). The component (F) is placed in the container A and/or the container B as required. For example, the kit may be composed of two forms: a liquid material and a powder material that are respectively a mixture of the components (A), (B) and (E) or the components (A), (B), (E) and (G) and a mixture of the components (C), (D) and (F). The component (B) is frequently liquid, and when the insoluble solid component (F) is contained in such liquid composition, the component (F) may be separated from the composition during long-term storage. For this reason, the component (F) is contained only in the powder material in the above case. Of course, it is a preferable embodiment of the invention that even if the total amount of the component (F) is contained in the liquid composition and is separated therefrom, these are placed in a dappen dish or the like and mixed together into a blend, and then a powder material not containing the component (F) is mixed. In such a preferable embodiment, as mentioned above, there is no particular problem even if the process takes time because the polymerization reaction does not proceed when the separated components are returned to a blend by mixing. On the contrary, that the component (F) which is used in larger parts by weight is not contained in the powder material provides an advantage that the composition containing the component (C) having a polymerization initiation action may be more quickly mixed with the liquid composition and thus the usable time is not shortened.

In an embodiment, in the container A is placed a liquid composition containing the component (AB) and optionally containing the component (E) and the component (G) as required; in the container C is placed a liquid composition containing the component ($B_O$), the component (C) and the component (D); and the component (F) is placed in the container A and/or the container C as required.

Needless to say, the combinations are not limited to these examples. The mixtures may be placed in separate containers, packed in a kit, and then provided as a product.

In another embodiment, the component (C) alone, the component (D) alone, and part or whole of the component (C)/component (D) may be contained in a jig that will be used to apply the dental curable composition on the tooth surface, and the jig is brought into contact with the components (A), (B), (E) and (F) immediately before use and thereby the dental curable composition is prepared before the patient and is applied to the tooth surface. The jig used to apply the dental curable composition to the tooth surface is not particularly limited and typical examples thereof include ink brushes, fiber balls or clothes, sponge balls, sponge pieces, mixing pads, and mixing dishes. These jigs may be used alone or in combination. When the component (C) alone, the component (D) alone and the components (C)/(D) are contained in the jig, an adsorbent or an embedding agent may be used appropriately to adsorb or fix these components to the jig.

Further, when the dental curable composition of the present invention is not in the form of a combination of liquid and powder materials but is a one-component paste composition that is a mixture of the components (A), (B), (C), (D), (E), (F) and (G), a known polymerization inhibitor may be contained in the range of 1 to 5000 ppm in the composition in order to ensure the storage stability. Such polymerization inhibitor is not particularly limited, but in general polymerization inhibitors and chain transfer agents for radically polymerizable monomers are preferable with examples including hydroquinone, hydroquinone monomethyl ether, 2,6-di-t-butyl-p-cresol, 4-t-butylcatechol and the like. The polymerization inhibitor may be used so long as the effect of the present invention is not impaired and may be preferably used in the range of 10 to 2000 ppm.

EXAMPLE

Hereinafter, the present invention will be explained by examples, but it should be understood that the scope of the present invention is not limited by these examples.

(Measurement Method for Curing Time and Polymerization Temperature)

In an aluminum pan, 0.1 g of the composition of the present invention was placed and the pan was set in a differential scanning calorimeter (DSC 22, manufactured by Seiko Instrument Inc.) in which the temperature was set constant at 37° C. in advance. The time from the start of polymerization to the maximum heat generation was defined and recorded as the curing time and the peak temperature at that time was defined and recorded as the polymerization temperature.

(Microtensile Bond Test)

A cylindrical cavity with a diameter $\phi$ of 4 mm was formed in a root of bovine tooth thawed immediately before the test, and thereby the root canal was enlarged. After moisture in the enlarged root canal was removed with an air gun, the composition of the present invention was applied in the cavity without treating the tooth surface. After the composition was allowed to stand in a thermostatic chamber at 37° C. and a relative humidity of 95% for 24 hours, the tooth was cut in halves along a flat surface passing through the center of the cylindrical cavity filled with the composition, parallel to the direction of the root canal. A 10 mm acrylic cube was bonded to the cut surface with Super-Bond C&B (manufactured by Sun Medical Co., Ltd.). After 20 minutes, the cube and the tooth were cut with a low-speed rotary diamond cutter (ISOMET, manufactured by Buehler Ltd.) to a thickness of about 1 mm, so that the cut surfaces were perpendicular to the direction of the root canal. Further, the piece was trimmed to a dumbbell shape (the thinnest part: the interface between the tooth and the filling composition) so that the bonding area was 1 mm$^2$. Then the microtensile bond strength test was carried out at a cross head speed of 1 mm/min using Compact Table-Top Universal Tester EZ-TEST (manufactured by Shimadzu Corporation).

(Sealing Property Test)

A cylindrical cavity with a diameter φ of 4 mm was formed in a root of bovine tooth thawed immediately before the test, and thereby the root canal was enlarged. After moisture in the enlarged root canal was removed with an air gun, the composition of the present invention was applied in the cavity without treating the tooth surface. After the composition was allowed to stand in a thermostatic chamber at 37° C. and a relative humidity of 95% for 24 hours, the tooth was cut vertical to the direction of the root canal using a low-speed rotary diamond cutter ISOMET so that the thickness was approximately 5 to 8 mm. The cut sample was immersed in a 5% aqueous solution of methylene blue for one hour, and was cut in halves along a flat surface passing through the center of the cylindrical cavity filled with the composition, parallel to the direction of the root canal. The composition was removed with a resin removal device and then the degree of dye penetration at the tooth substance interface was evaluated. Further, the sealing properties were also evaluated with the composition that had been allowed to stand in a thermostatic chamber at 37° C. and a relative humidity of 95% for 24 hours (37° C. for one day) and had been subjected to a thermal cycle test consisting of 5000 cycles at 5 to 55° C. (TC 5000) (thermal hysteresis)

The evaluation criteria were classified as follows by rounding off a value obtained by dividing the dye-stained area by the whole bonding area to two decimal places. Very good: 0, Good: to 0.20, Do: 0.21 to 0.50, Poor: 0.51 to 0.80, Very poor: 0.81 to 1.0

(0 shows that no dye penetration was observed.)

(Calculation of Photo-Polymerization Degree)

The compositions of the present invention before and after light irradiation were analyzed by an attenuated total reflection method (ATR method) using an FT-IR (Fourier Transform-Infrared Spectrometer). The polymerization degree (%) was calculated with ratios of the height of the peaks assigned to C=C at around 1640 cm$^{-1}$ and to C=O at around 1710 cm$^{-1}$. The calculation method is shown below.

The polymerization degree (%) (1=Ra/Rb)×100
Ra: the peak height ratio after light irradiation (C=C/C=O)
Rb: the peak height ratio before light irradiation (C=C/C=O)

The meanings of the abbreviations described in the following examples and comparative examples are as follows.

4-MET: 4-methacryloyloxyethyltrimellitic acid (Component AB)
4-META: 4-methacryloyloxyethyltrimellitic anhydride (Component AB)
PM: 2-methacryloyloxyethyl acid phosphate (Component AB)
P-2M: bis(2-methacryloyloxyethyl) acid phosphate (Component AB)
HEMA: 2-hydroxyethylmethacrylate (Component $B_0$)
VR90: bisphenol A diglycidyl ester diacrylate (Component $B_0$)
2.6E: 2,2-bis(4-methacryloyloxypolyethoxyphenyl)propane (Component $B_0$)
3G: triethylene glycol dimethacrylate (Component $B_0$)
A-9300: ethoxylated isocyanuric acid triacrylate (Component $B_0$)
UDMA: urethanedimethacrylate (Component $B_0$)
A-DPH: dipentaerythritol hexaacrylate (Component $B_0$)
NPG: N-phenylglycine (Component C and component A (component (CA)))
NPG-Na: N-phenylglycine sodium salt (Component C)
NPG-K: N-phenylglycine potassium salt (Component C)
p-TSNa: sodium p-toluenesulfinate (Component D)
DTMPO: 2,4,6-trimethylbenzoyldiphenylphosphine oxide (Component G)
CQ: camphorquinone (Component G)
DEPT: diethanol-p-toluidine
BPO: benzoyl peroxide (organic peroxide)

Example 1

A dental curable composition of the present invention was prepared by mixing and dissolving a liquid material including 18.5 parts by weight of 4-MET, 37.0 parts by weight of 2-hydroxyethylmethacrylate (HEMA), 13.8 parts by weight of bisphenol A diglycidyl ester diacrylate (VR90), 13.8 parts by weight of 2,2-bis(4-methacryloyloxypolyethoxyphenyl)propane (2.6E) and 9.3 parts by weight of triethylene glycol dimethacrylate (3G), and a powder material including 7.1 parts by weight of N-phenylglycine (NPG) and 0.5 part by weight of sodium p-toluenesulfinate (p-TSNa). The dental curable composition was used immediately after prepared, and the curing time and polymerization temperature were measured by DSC. The sealing test was also carried out. As a result, the dental curable composition had a curing time of 12.0 minutes and a polymerization temperature of 37.4° C. The sealing property was good with the dye penetration being 0.5 or less even after the TC 5000 test.

The amounts of the components and the test results of the dental curable composition are shown in Table 1.

Example 2

A dental curable composition of the present invention was prepared by mixing and dissolving a liquid material including 18.5 parts by weight of 4-MET, 37.0 parts by weight of HEMA, 13.8 parts by weight of VR90, 13.8 parts by weight of 2.6E and 9.3 parts by weight of 3G, and a powder material including 7.1 parts by weight of N-phenylglycine sodium salt (NPG-Na) and 0.5 part by weight of p-TSNa. The dental curable composition was used immediately after prepared, and the curing time and polymerization temperature were measured by DSC. The sealing test was also carried out. As a result, the dental curable composition had a curing time of 13.0 minutes and a polymerization temperature of 37.5° C. The sealing property was good with the dye penetration being 0.5 or less even after the TC 5000 test.

The amounts of the components and the test results of the dental curable composition are shown in Table 1.

Example 3

A dental curable composition of the present invention was prepared by mixing and dissolving a liquid material including 18.5 parts by weight of 4-MET, 37.0 parts by weight of HEMA, 13.8 parts by weight of ethoxylated isocyanuric acid triacrylate (A-9300), 13.8 parts by weight of 2.6E, 4.1 parts by weight of 3G and 5.2 parts by weight of distilled water, and a powder material including 7.1 parts by weight of NPG-Na and 0.5 part by weight of p-TSNa. The dental curable composition was used immediately after prepared, and the curing time and polymerization temperature were measured by DSC. The microtensile bond strength test and the sealing test were also carried out. As a result, the dental curable composition had a curing time of 11.5 minutes, a polymerization temperature of 37.4° C. and a microtensile bond strength of 5.1 MPa. The sealing property was excellent with the dye penetration being 0.2 or less both after one day at 37° C. and after the TC 5000 test.

The amounts of the components and the test results of the dental curable composition are shown in Table 1.

Example 4

A dental curable composition of the present invention was prepared by mixing and dissolving a liquid material including 18.5 parts by weight of 4-META, 37.0 parts by weight of HEMA, 13.8 parts by weight of A-9300, 13.8 parts by weight of 2.6E, 4.1 parts by weight of 3G and 5.2 parts by weight of distilled water, and a powder material including 7.1 parts by weight of N-phenylglycine potassium salt (NPG-K) and 0.5 part by weight of p-TSNa. The dental curable composition was used immediately after prepared, and the curing time and polymerization temperature were measured by DSC. The microtensile bond strength test and the sealing test were also carried out. As a result, the dental curable composition had a curing time of 12.2 minutes, a polymerization temperature of 37.6° C. and a microtensile bond strength of 4.8 MPa. The sealing property was excellent with the dye penetration being 0.2 or less both after one day at 37° C. and after the TC 5000 test.

The amounts of the components and the test results of the dental curable composition are shown in Table 1.

Example 5

A dental curable composition of the present invention was prepared by mixing a liquid material including 9.9 parts by weight of 4-MET, 9.9 parts by weight of HEMA, 12.4 parts by weight of A-9300, 9.9 parts by weight of glycerin dimethacrylate (GDMA) and 7.1 parts by weight of 3G, and a powder material including 3.6 parts by weight of NPG-Na, 0.3 part by weight of p-TSNa, 40.6 parts by weight of zirconium oxide with an average particle size of 2 µm and 6.3 parts by weight of spherical silica with an average particle size of 5 µm, on a mixing pad. The curing time and polymerization temperature after one minute from the start of the mixing were measured by DSC. The microtensile bond strength test and the sealing test were also carried out. As a result, the dental curable composition had a curing time of 7.5 minutes, a polymerization temperature of 37.3° C. and a microtensile bond strength of 6.7 MPa. The sealing property was excellent, that is, no dye penetration was observed after one day at 37° C. and the dye penetration was 0.2 or less even after the TC 5000 test.

The amounts of the components and the test results of the dental curable composition are shown in Table 1.

Example 6

A dental curable composition of the present invention was prepared by mixing a liquid material including 9.6 parts by weight of 4-MET, 9.6 parts by weight of HEMA, 12.1 parts by weight of A-9300, 9.6 parts by weight of VR90, 6.6 parts by weight of 3G and 3.0 parts by weight of distilled water, and a powder material including 3.6 parts by weight of NPG-Na, 0.3 part by weight of p-TSNa, 39.4 parts by weight of zirconium oxide with an average particle size of 2 µm and 6.2 parts by weight of spherical silica with an average particle size of 5 µm, on a mixing pad. The curing time and polymerization temperature after one minute from the start of the mixing were measured by DSC. The microtensile bond strength test and the sealing test were also carried out. As a result, the dental curable composition had a curing time of 7.0 minutes, a polymerization temperature of 37.5° C. and a microtensile bond strength of 6.7 MPa. The sealing property was excellent, that is, no dye penetration was observed after one day at 37° C. and the dye penetration was 0.2 or less even after the TC 5000 test.

The amounts of the components and the test results of the dental curable composition are shown in Table 1.

Example 7

A dental curable composition of the present invention was prepared by mixing a liquid material including 9.6 parts by weight of 4-META, 9.6 parts by weight of HEMA, 12.1 parts by weight of A-9300, 9.6 parts by weight of urethanedimethacrylate (UDMA), 6.6 parts by weight of 3G and 3.0 parts by weight of distilled water, and a powder material including 3.6 parts by weight of NPG-K, 0.3 part by weight of p-TSNa, 39.4 parts by weight of zirconium oxide with an average particle size of 2 µm and 6.2 parts by weight of spherical silica with an average particle size of 5 µm, on a mixing pad. The curing time and polymerization temperature after one minute from the start of the mixing were measured by DSC. The microtensile bond strength test and the sealing test were also carried out. As a result, the dental curable composition had a curing time of 6.8 minutes, a polymerization temperature of 37.6° C. and a microtensile bond strength of 8.8 MPa. The sealing property was excellent, that is, no dye penetration was observed even after one day at 37° C. and after the TC 5000 test.

The amounts of the components and the test results of the dental curable composition are shown in Table 1.

Example 8

A dental curable composition of the present invention was prepared by mixing and dissolving a liquid material including 18.1 parts by weight of 4-META, 18.1 parts by weight of HEMA, 22.8 parts by weight of A-9300, 18.1 parts by weight of GDMA and 13.3 parts by 2.6E, and a powder material including 8.6 parts by weight of NPG-K and 1.0 part by weight of p-TSNa. The dental curable composition was used immediately after prepared, and the curing time and polymerization temperature were measured by DSC. The sealing test was also carried out. As a result, the dental curable composition had a curing time of 6.7 minutes and a polymerization temperature of 37.5° C. The sealing property was good, that is, the dye penetration was 0.5 or less even after the TC 5000 test.

The amounts of the components and the test results of the dental curable composition are shown in Table 1.

Example 9

A dental curable composition of the present invention was prepared by mixing and dissolving a liquid material including 17.3 parts by weight of 4-MET, 17.3 parts by weight of HEMA, 21.8 parts by weight of dipentaerythritolhexaacrylate (A-DPH), 17.3 parts by weight of GDMA, 12.7 parts by weight of 3G, 4.4 parts by weight of distilled water and 0.1 part by weight of camphorquinone (CQ), and a powder material including 8.2 parts by weight of NPG-Na and 0.9 part by weight of p-TSNa. The dental curable composition was used immediately after prepared, and the curing time and polymerization temperature were measured by DSC. The microtensile bond strength test and the sealing test were also carried out. As a result, the dental curable composition had a curing time of 6.2 minutes, a polymerization temperature of 37.4° C. and a microtensile bond strength of 4.1 MPa. The sealing property was good, that is, the dye penetration was 0.2 or less both after one day at 37° C. and after the TC 5000 test.

The amounts of the components and the test results of the dental curable composition are shown in Table 1.

Example 10

A dental curable composition of the present invention was prepared by mixing a liquid material including 9.0 parts by weight of 4-MET, 9.0 parts by weight of HEMA, 11.3 parts by weight of A-9300, 8.9 parts by weight of GDMA, 6.6 parts by weight of 2.6E and 2.4 parts by weight of distilled water, and a powder material including 4.2 parts by weight of NPG-Na, 0.5 part by weight of p-TSNa, 41.5 parts by weight of zirconium oxide with an average particle size of 2 μm and 6.6 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 6.1 minutes, a polymerization temperature of 37.3° C. and a microtensile bond strength of 12.1 MPa. The sealing property was excellent, that is, no dye penetration was observed even after one day at 37° C. and after the TC 5000 test.

The amounts of the components and the test results of the dental curable composition are shown in Table 1.

Example 1

A dental curable composition of the present invention was prepared by mixing a liquid material including 9.5 parts by weight of 4-MET, 9.5 parts by weight of HEMA, 12.0 parts by weight of A-9300, 9.5 parts by weight of GDMA, 7.0 parts by weight of 2.6E, 2.5 parts by weight of distilled water, 0.01 part by weight of CQ and 0.01 part by weight of 2,4,6-trimethylbenzoyldiphenylphosphine oxide (DTMPO), and a powder material including 4.0 parts by weight of NPG-Na, 0.3 part by weight of p-TSNa, 40.0 parts by weight of zirconium oxide with an average particle size of 2 μm and 6.18 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 6.0 minutes, a polymerization temperature of 37.4° C. and a microtensile bond strength of 12.8 MPa. The sealing property was excellent, that is, no dye penetration was observed even after one day at 37° C. and after the TC 5000 test.

The amounts of the components and the test results of the dental curable composition are shown in Table 1.

Example 12

A dental curable composition of the present invention was prepared by mixing a liquid material including 9.0 parts by weight of 4-MET, 8.9 parts by weight of HEMA, 11.3 parts by weight of A-9300, 8.9 parts by weight of GDMA, 6.6 parts by weight of 2.6E, 2.4 parts by weight of distilled water and 0.1 part by weight of CQ, and a powder material including 4.2 parts by weight of NPG-Na, 0.5 part by weight of p-TSNa, 41.5 parts by weight of zirconium oxide with an average particle size of 2 μm and 6.6 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 6.0 minutes, a polymerization temperature of 37.5° C. and a microtensile bond strength of 12.4 MPa. The sealing property was excellent, that is, no dye penetration was observed even after one day at 37° C. and after the TC 5000 test.

The amounts of the components and the test results of the dental curable composition are shown in Table 1.

Example 13

A dental curable composition of the present invention was prepared by mixing a liquid material including 9.9 parts by weight of 4-MET, 8.0 parts by weight of HEMA, 13.3 parts by weight of A-9300, 6.9 parts by weight of UDMA, 6.6 parts by weight of 2.6E and 3.3 parts by weight of distilled water, and a powder material including 4.0 parts by weight of NPG-Na, 0.5 part by weight of p-TSNa, 41.5 parts by weight of zirconium oxide with an average particle size of 2 μm and 6.0 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 6.3 minutes, a polymerization temperature of 37.5° C. and a microtensile bond strength of 11.1 MPa. The sealing property was excellent, that is, no dye penetration was observed even after one day at 37° C. and after the TC 5000 test.

The amounts of the components and the test results of the dental curable composition are shown in Table 1.

Example 14

A dental curable composition of the present invention was prepared by mixing a liquid material including 10.0 parts by weight of 2-methacryloyloxyethyl acid phosphate (PM), 8.0 parts by weight of HEMA, 13.3 parts by weight of A-9300, 6.9 parts by weight of 2.6E, 6.6 parts by weight of 2.6E, 3.1 parts by weight of distilled water, 0.05 part by weight of CQ and 0.05 part by weight of DTMPO, and a powder material including 4.0 parts by weight of NPG-Na, 0.5 part by weight of p-TSNa, 41.5 parts by weight of zirconium oxide with an average particle size of 2 μm and 6.0 parts by weight of spherical silica with an average particle size of 5 μm, on a mixing pad. The curing time and polymerization temperature after one minute from the start of the mixing were measured by DSC. In addition, the microtensile bond strength test and the sealing test were also carried out. As a result, the dental curable composition had a curing time of 5.7 minutes, a polymerization temperature of 37.5° C. and a microtensile bond strength of 13.2 MPa. The sealing property was excellent, that is, no dye penetration was observed even after one day at 37° C. and after the TC 5000 test.

The amounts of the components and the test results of the dental curable composition are shown in Table 1.

Example 15

A dental curable composition of the present invention was prepared by mixing a liquid material including 5.9 parts by weight of 4-MET, 4.0 parts by weight of bis(2-methacryloyloxyethyl)acid phosphate (P-2M), 8.0 parts by weight of HEMA, 13.3 parts by weight of A-DPH, 6.9 parts by weight of 2.6E, 6.6 parts by weight of UDMA, 3.1 parts by weight of distilled water, 0.1 part by weight of CQ and 0.1 part by weight of DTMPO, and a powder material including 4.0 parts by weight of NPG-Na, 0.5 part by weight of p-TSNa, 41.5 parts by weight of zirconium oxide with an average particle size of 2 μm and 6.0 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 5.6 minutes, a polymerization temperature of 37.4° C. and a microtensile bond strength of 10.7 MPa. The sealing property was excellent, that is, no dye penetration was observed even after one day at 37° C. and after the TC 5000 test.

The amounts of the components and the test results of the dental curable composition are shown in Table 1.

Example 16

A dental curable composition of the present invention was prepared by mixing a liquid material including 9.3 parts by weight of 4-META, 8.7 parts by weight of HEMA, 10.8 parts by weight of A-9300, 2.1 parts by weight of 3G, 3.6 parts by weight of UDMA and 3.4 parts by weight of distilled water, and a powder material including 4.2 parts by weight of NPG-Na, 0.5 part by weight of p-TSNa, 50.4 parts by weight of zirconium oxide with an average particle size of 2 μm and 7.0 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 5.9 minutes, a polymerization temperature of 37.7° C. and a microtensile bond strength of 10.9 MPa. The sealing property was excellent, that is, no dye penetration was observed even after one day at 37° C. and after the TC 5000 test.

The amounts of the components and the test results of the dental curable composition are shown in Table 1.

Example 17

A dental curable composition of the present invention was prepared by mixing a liquid material including 9.3 parts by weight of 4-META, 8.7 parts by weight of HEMA, 10.8 parts by weight of A-9300, 2.1 parts by weight of 3G, 3.6 parts by weight of UDMA, 3.4 parts by weight of distilled water and 0.1 part by weight of CQ, and a powder material including 4.2 parts by weight of NPG-Na, 0.5 part by weight of p-TSNa, 50.3 parts by weight of zirconium oxide with an average particle size of 2 μm and 7.0 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 5.8 minutes, a polymerization temperature of 37.6° C. and a microtensile bond strength of 9.8 MPa. The sealing property was excellent, that is, no dye penetration was observed even after one day at 37° C. and after the TC 5000 test.

Comparative Example 1

In Example 1, diethanol p-toluidine (DEPT) and benzoyl peroxide (BPO) were used without using NPG-Na and p-TSNa. As a result, the dental curable composition had a curing time of 3.8 minutes and a polymerization temperature of 41.8° C. The microtensile bond strength was unable to be tested because there occurred the peeling of the composition from the bond interface during the stage of preparing the test pieces. In addition, for the sealing property, dye penetration was observed both after one day at 37° C. and after the TC 5000 test.

The amounts of the components and the test results of the dental curable composition are shown in Table 2.

Comparative Example 2

In Example 5, diethanol p-toluidine (DEPT) and BPO were used without using NPG-Na and p-TSNa. As a result, the dental curable composition had a curing time of 4.3 minutes and a polymerization temperature of 42.2° C. The microtensile bond strength was unable to be tested because there occurred the peeling of the composition from the bond interface during the stage of preparing the test pieces. In addition, for the sealing property, dye penetration was observed both after one day at 37° C. and after the TC 5000 test.

The amounts of the components and the test results of the dental curable composition are shown in Table 2.

Comparative Example 3

In Example 15, diethanol p-toluidine (DEPT) was used without using NPG-K. In addition, 0.3 parts by weight of BPO was added and the amount of spherical silica with an average particle size of 5 μm was changed to 5.7 parts by weight. As a result, the dental curable composition had a curing time of 3.2 minutes and a polymerization temperature of 42.6° C. The microtensile bond strength was unable to be tested because the composition debonded from the test pieces during the storage under static conditions in a constant temperature bath at 37° C. for 24 hours. In addition, for the sealing property, dye penetration was observed both after one day at 37° C. and after the TC 5000 test.

The amounts of the components and the test results of the dental curable composition are shown in Table 2.

Comparative Example 4

In Example 16, 4.2 parts by weight of diethanol p-toluidine (DEPT) was used without using NPG-Na. In addition, 1.0 part by weight of BPO was added and the amounts of zirconium oxide and spherical silica with an average particle size of 5 μm were changed to 50.4 and 6.0 parts by weight, respectively. As a result, the dental curable composition had a curing time of 2.6 minutes and a polymerization temperature of 42.8° C. The microtensile bond strength was unable to be tested because the composition debonded from the test pieces during the storage under static conditions in a constant temperature bath at 37° C. for 24 hours. In addition, for the sealing property, dye penetration was observed both after one day at 37° C. and after the TC 5000 test.

The amounts of the components and the test results of the dental curable composition are shown in Table 2.

TABLE 1

| | Dental Curable Composition (parts by weight) | | | | | | | | | |
|---|---|---|---|---|---|---|---|---|---|---|
| | (AB) | (B₀) | | | | (C) or (CA) | (D) | (E) | (F) | |
| Ex. 1 | 4-MET (18.5) | HEMA (37.0) | VR90 (13.8) | 2.6E (13.8) | 3G (9.3) | NPG* (7.1) | P-TSNa (0.5) | — | — | |
| Ex. 2 | 4-MET (18.5) | HEMA (37.0) | VR90 (13.8) | 2.6E (13.8) | 3G (9.3) | NPG-Na (7.1) | P-TSNa (0.5) | — | | |
| Ex. 3 | 4-MET (18.5) | HEMA (37.0) | A-9300 (13.8) | 2.6E (13.8) | 3G (4.1) | NPG-Na (7.1) | P-TSNa (0.5) | H₂O (5.2) | — | |
| Ex. 4 | 4-META (18.5) | HEMA (37.0) | A-9300 (13.8) | 2.6E (13.8) | 3G (4.1) | NPG-K (7.1) | P-TSNa (0.5) | H₂O (5.2) | — | |
| Ex. 5 | 4-MET (9.9) | HEMA (9.9) | A-9300 (12.4) | GDMA (9.9) | 3G (7.1) | MPG-Na (3.6) | P-TSNa (0.3) | — | ZrO₂ (40.6) | SiO₂ (6.3) |
| Ex. 6 | 4-MET (9.6) | HEMA (9.6) | A-9300 (12.1) | VR90 (9.6) | 3G (6.6) | NPG-Na (3.6) | P-TSNa (0.3) | H₂O (3.0) | ZrO₂ (39.4) | SiO₂ (6.2) |
| Ex. 7 | 4-META (9.6) | HEMA (9.6) | A-9300 (12.1) | UDMA (9.6) | 3G (6.6) | NPG-K (3.6) | P-TSNa (0.3) | H₂O (3.0) | ZrO₂ (39.4) | SiO₂ (6.2) |
| Ex. 8 | 4-META (18.1) | HEMA (18.1) | A-9300 (22.8) | GDMA (18.1) | 2.6E (13.3) | NPG-K (8.6) | P-TSNa (1.0) | — | — | |
| Ex. 9 | 4-MET (17.3) | HEMA (17.3) | A-DPH (21.8) | GDMA (17.3) | 3G (12.7) | NPG-Na (8.2) | P-TSNa (0.9) | H₂O (4.4) | — | |
| Ex. 10 | 4-MET (9.0) | HEMA (9.0) | A-9300 (11.3) | GDMA (8.9) | 2.6E (6.6) | NPG-Na (4.2) | P-TSNa (0.5) | H₂O (2.4) | ZrO₂ (41.5) | SiO₂ (6.6) |
| Ex. 11 | 4-MET (9.5) | HEMA (9.5) | A-9300 (12.0) | GDMA (9.5) | 2.6E (7.0) | NPG-Na (4.0) | P-TSNa (0.3) | H₂O (2.5) | ZrO₂ (40.0) | SiO₂ (6.18) |
| Ex. 12 | 4-MET (9.0) | HEMA (8.9) | A-9300 (11.3) | GDMA (8.9) | 2.6E (6.6) | NPG-Na (4.2) | P-TSNa (0.5) | H₂O (2.4) | ZrO₂ (41.5) | SiO₂ (6.6) |
| Ex. 13 | 4-MET (9.9) | HEMA (8.0) | A-9300 (13.3) | 2.6E (6.9) | UDMA (6.6) | NPG-Na (4.0) | P-TSNa (0.5) | H₂O (3.3) | ZrO₂ (41.5) | SiO₂ (6.0) |
| Ex. 14 | PM (10.0) | HEMA (8.0) | A-9300 (13.3) | 2.6E (6.9) | 3G (6.6) | NPG-Na (4.0) | P-TSNa (0.5) | H₂O (3.1) | ZrO₂ (41.5) | SiO₂ (6.0) |
| Ex. 15 | 4-MET (5.9) P-2M (4.0) | HEMA (8.0) | A-DPH (13.3) | 2.6E (6.9) | UDMA (6.6) | NPG-K (4.0) | P-TSNa (0.5) | H₂O (3.1) | ZrO₂ (41.5) | SiO₂ (6.0) |
| Ex. 16 | 4-META (9.3) | HEMA (8.7) | A-9300 (10.8) | 3G (2.1) | UDMA (3.6) | NPG-Na (4.2) | P-TSNa (0.5) | H₂O (3.4) | ZrO₂ (50.4) | SiO₂ (7.0) |
| Ex. 17 | 4-META (9.3) | HEMA (8.7) | A-9300 (10.8) | 3G (2.1) | UDMA (3.6) | NPG-Na (4.2) | P-TSNa (0.5) | H₂O (3.4) | ZrO₂ (50.3) | SiO₂ (7.0) |

| | Dental Curable Composition (parts by weight) | | *1 | *2 | *3 | *4 | |
|---|---|---|---|---|---|---|---|
| | (G) | | | | | 30° C. 1 day | TC 5000 |
| Ex. 1 | — | | 12.0 | 37.4 | — | Good | Do |
| Ex. 2 | — | | 13.0 | 37.5 | — | Do | Do |
| Ex. 3 | — | | 11.5 | 37.4 | 5.1 | Good | Good |
| Ex. 4 | — | | 12.2 | 37.6 | 4.8 | Good | Good |
| Ex. 5 | — | | 7.5 | 37.3 | 6.7 | Very Good | Good |
| Ex. 6 | — | | 7.0 | 37.5 | 8.4 | Very Good | Very Good |
| Ex. 7 | — | | 6.8 | 37.6 | 8.8 | Very Good | Very Good |
| Ex. 8 | — | | 6.7 | 37.5 | — | Do | Do |
| Ex. 9 | CQ (0.1) | | 6.2 | 37.4 | 4.1 | Good | Good |
| Ex. 10 | — | | 6.1 | 37.3 | 12.1 | Very Good | Very Good |
| Ex. 11 | CQ (0.01) | DTMPO (0.01) | 6.0 | 37.4 | 12.8 | Very Good | very Good |
| Ex. 12 | CQ (0.1) | | 6.0 | 37.5 | 12.4 | Very Good | Very Good |
| Ex. 13 | — | | 6.3 | 37.5 | 11.1 | Very Good | Very Good |
| Ex. 14 | CQ (0.05) | DTMPO (0.05) | 5.7 | 37.5 | 13.2 | Very Good | Very Good |
| Ex. 15 | CQ (0.1) | DTMPO (0.1) | 5.6 | 37.4 | 10.7 | Very Good | Very Good |

TABLE 1-continued

| | | Curing time (Min) | Polymerization temperature (°C.) | Microtensile bond strength (MPa) | Sealing Property 37° C. for one day | TC5000 |
|---|---|---|---|---|---|---|
| Ex. 16 | — | 5.9 | 37.7 | 10.9 | Very Good | Very Good |
| Ex. 17 | CQ (0.1) | 5.8 | 37.6 | 9.8 | Very Good | Very Good |

*1: Curing time (min)
*2: Polymerization temperature (° C.)
*3: Microtensile bond strength (MPa)
*4: Sealing property

TABLE 2

| | Comparative curable composition (parts by weight) | | Curing time (Min) | Polymerization temperature (° C.) | Microtensile bond strength (MPa) | Sealing Property 37° C. for one day | TC5000 |
|---|---|---|---|---|---|---|---|
| Comparative Example 1 | Component AB | 4-MET(18.5) | 3.8 | 41.8 | Test pieces could not be prepared | Poor | Very poor |
| | Component B₀ | HEMA(37.0), VR90(13.8), 2.6E(13.8), 3G(9.3) | | | | | |
| | Component C | DEPT(7.1) | | | | | |
| | Component D | — | | | | | |
| | Component E | — | | | | | |
| | component F | — | | | | | |
| | Component G | — | | | | | |
| | | BPO(0.5) | | | | | |
| Comparative Example 2 | Component AB | 4-MET(9.9) | 4.3 | 42.2 | Test pieces could not be prepared | Very poor | Very poor |
| | component B₀ | HEMA(9.9), A-9300(12.4), GDMA(9.9), 3G(7.1) | | | | | |
| | Component C | DEPT(3.6) | | | | | |
| | Component D | — | | | | | |
| | Component E | — | | | | | |
| | component F | ZrO2(40.6), SiO2(6.3) | | | | | |
| | Component G | — | | | | | |
| | | BPO(0.3) | | | | | |
| Comparative Example 3 | Component AB | 4-MET(5.9), P-2M(4.0) | 3.3 | 42.6 | Debonded | Do | Very poor |
| | component B₀ | HEMA(8.0), A-DTP(13.3), 2.6E(6.9), UDMA(6.6) | | | | | |
| | Component C | DEPT(4.0) | | | | | |
| | Component D | P-TSNa(0.5) | | | | | |
| | Component E | H2O(3.1) | | | | | |
| | component F | ZrO2(41.5), SiO2(5.7) | | | | | |
| | Component G | CQ(0.1), DTMPO(0.1) | | | | | |
| | | BPO(0.3) | | | | | |
| Comparative Example 4 | Component AB | 4-META(9.3) | 2.6 | 42.8 | 1.7 | Poor | Very poor |
| | component B₀ | HEMA(8.7), A-9300(10.8), 3G(2.1), UDMA(3.6) | | | | | |
| | Component C | DEPT(4.2) | | | | | |
| | Component D | P-TSNa(0.5) | | | | | |
| | Component E | H2O(3.4) | | | | | |
| | component F | ZrO2(50.4), SiO2(6.0) | | | | | |
| | Component G | — | | | | | |
| | | BPO(1.0) | | | | | |

As shown in Table 1 and Table 2, the dental curable compositions of the present invention may be polymerized even when they do not contain peroxide as a polymerization initiator. Further, the compositions can be polymerized without inhibition by water even under wet conditions, and the heat of polymerization is nearly equal to the body temperature. The dental curable compositions have excellent adhesion to teeth without surface treatment, cause no gaps in the bonding interface and have excellent decomposition resistance. Therefore, they are not only extremely useful as a dental cement but also may greatly contribute to dental care.

Example 18

A dental curable composition of the present invention was prepared by mixing and dissolving a liquid material including 0.5 part by weight of phosphoric acid, 47.0 parts by weight of 2-hydroxyethylmethacrylate (HEMA), 22.2 parts by weight of glycerinedimethacrylate (GDMA) and 23.0 parts by weight of 2,2-bis(4-methacryloyloxypolyethoxyphenyl)propane (2.6E), and a powder composition including 6.8 parts by weight of N-phenylglycine potassium (NPG-K) and 0.5 part by weight of sodium p-toluenesulfinate (p-TSNa). The dental curable composition was used immediately after prepared, and the curing time and polymerization temperature were measured by DSC. The sealing test was also carried out. As a result, the dental curable composition had a curing time of 68.0 minutes and a polymerization temperature of 37.6° C. The sealing property was good with the dye penetration being 0.5 or less after the TC 5000 test.

The amounts of the components and the test results of the dental curable composition are shown in Table 3.

Example 19

A dental curable composition of the present invention was prepared by mixing and dissolving a liquid material including 1.0 part by weight of citric acid, 47.0 parts by weight of HEMA, 20.8 parts by weight of GDMA, 13.8 parts by weight of 2.6E, 8.9 parts by weight of 3G and 3.0 parts by weight of distilled water, and a powder material including 5.0 parts by weight of N-phenylglycine sodium (NPG-Na) and 0.5 part by weight of p-TSNa. The dental curable composition was used immediately after prepared, and the curing time and polymerization temperature were measured by DSC. The microtensile bond strength test and the sealing test were also carried out. As a result, the dental curable composition had a curing time of 10.1 minutes, a polymerization temperature of 37.5° C. and a microtensile bond strength of 6.1 MPa. The sealing property was excellent with the dye penetration being 0.2 or less both after one day at 37° C. and after the TC 5000 test.

The amounts of the components and the test results of the dental curable composition are shown in Table 3.

Example 20

A dental curable composition of the present invention was prepared by mixing and dissolving a liquid material including 1.0 part by weight of lactic acid, 47.0 parts by weight of HEMA, 21.3 parts by weight of ethoxylated isocyanuric acid triacrylate (A-9300), 13.8 parts by weight of 2.6E, 8.1 parts by weight of 3G and 1.2 parts by weight of distilled water, and a powder material including 7.1 parts by weight of NPG-K and 0.5 part by weight of p-TSNa. The dental curable composition was used immediately after prepared, and the curing time and polymerization temperature were measured by DSC. The microtensile bond strength test and the sealing test were also carried out. As a result, the dental curable composition had a curing time of 47.3 minutes, a polymerization temperature of 37.8° C. and a microtensile bond strength of 5.3 MPa. The sealing property was good with the dye penetration being 0.5 or less both after one day at 37° C. and after the TC 5000 test.

The amounts of the components and the test results of the dental curable composition are shown in Table 3.

Example 21

A dental curable composition of the present invention was prepared by mixing and dissolving a liquid material including 10.0 parts by weight of ascorbic acid, 40.5 parts by weight of HEMA, 15.0 parts by weight of A-9300, 15.0 parts by weight of 2.6E, 4.0 parts by weight of 3G and 10.0 parts by weight of distilled water, and a powder material including 5.0 parts by weight of N-phenylglycine (NPG) and 0.5 part by weight of p-TSNa. The dental curable composition was used immediately after prepared, and the curing time and polymerization temperature were measured by DSC. The microtensile bond strength test and the sealing test were also carried out. As a result, the dental curable composition had a curing time of 50.2 minutes, a polymerization temperature of 37.6° C. and a microtensile bond strength of 3.6 MPa. The sealing property was good with the dye penetration being 0.5 or less both after one day at 37° C. and after the TC 5000 test.

The amounts of the components and the test results of the dental curable composition are shown in Table 3.

Example 22

A dental curable composition of the present invention was prepared by mixing a liquid material including 1.0 part by weight of phosphoric acid, 19.8 parts by weight of HEMA, 12.2 parts by weight of A-9300, 10.5 parts by weight of GDMA and 5.2 parts by weight of 3G, and a powder material including 4.0 parts by weight of NPG-Na, 0.3 part by weight of p-TSNa, 40.8 parts by weight of zirconium oxide with an average particle size of 2 μm and 6.5 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 61.0 minutes, a polymerization temperature of 37.4° C. and a microtensile bond strength of 4.7 MPa. The sealing property was good with the dye penetration being 0.5 or less even after one day at 37° C. and after the TC 5000 test.

The amounts of the components and the test results of the dental curable composition are shown in Table 3.

Example 23

A dental curable composition of the present invention was prepared by mixing a liquid material including 0.98 part by weight of citric acid, 19.6 parts by weight of HEMA, 12.4 parts by weight of A-9300, 10.5 parts by weight of GDMA, 1.5 parts by weight of 3G, 3.5 parts by weight of distilled water, 0.01 part by weight of camphorquinone (CQ) and 0.01 part by weight of 2,4,6-trimethylbenzoyldiphenylphosphine oxide (DTMPO), and a powder material including 4.0 parts by weight of NPG-Na, 0.5 part by weight of p-TSNa, 40.5 parts by weight of zirconium oxide with an average particle size of 2 μm and 6.5 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 9.0 minutes, a polymerization temperature of 37.5° C. and a microtensile bond strength of 7.7 MPa. The sealing property was excellent, that is, no dye penetration was observed after one day at 37° C. and the dye penetration was 0.2 or less even after the TC 5000 test.

The amounts of the components and the test results of the dental curable composition are shown in Table 3.

Example 24

A dental curable composition of the present invention was prepared by mixing a liquid material including 0.5 part by weight of lactic acid, 9.6 parts by weight of HEMA, 12.4 parts by weight of A-9300, 19.6 parts by weight of urethanedimethacrylate (UDMA), 6.6 parts by weight of 3G and 3.0 parts by weight of distilled water, and a powder material including 3.6 parts by weight of NPG-K, 0.3 part by weight of p-TSNa, 39.4 parts by weight of zirconium oxide with an average particle size of 2 μm and 5.0 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 45.8 minutes, a polymerization temperature of 37.7° C. and a microtensile bond strength of 4.8 MPa. The sealing property was excellent with the dye penetration being 0.2 or less both after one day at 37° C. and after the TC 5000 test.

The amounts of the components and the test results of the dental curable composition are shown in Table 3.

Example 25

A dental curable composition of the present invention was prepared by mixing and dissolving a liquid material including 0.1 part by weight of ascorbic acid, 13.5 parts by weight of HEMA, 13.8 parts by weight of A-9300, 15.2 parts by weight of GDMA and 3.3 parts by weight of 2.6E, and a powder material including 8.6 parts by weight of NPG, 1.0 part by weight of p-TSNa, 40.0 parts by weight of zirconium oxide with an average particle size of 2 μm and 4.5 parts by weight of spherical silica with an average particle size of 5 μm. The dental curable composition was used immediately after prepared, and the curing time and polymerization temperature were measured by DSC. The sealing test was also carried out. The dental curable composition had a curing time of 48.1 minutes and a polymerization temperature of 37.6° C. The sealing property was good, that is, the dye penetration was 0.2 or less after one day at 37° C. and the dye penetration was 0.5 or less even after the TC 5000 test.

The amounts of the components and the test results of the dental curable composition are shown in Table 3.

Comparative Example 5

In Example 18, 6.8 parts by weight of diethanol p-toluidine (DEPT) and 0.5 part by weight of benzoyl peroxide (BPO) were used without using NPG-K and p-TSNa. As a result, the dental curable composition had a curing time of 2.8 minutes and a polymerization temperature of 43.7° C. The microtensile bond strength was unable to be tested because there occurred the peeling of the composition from the bond interface during the stage of preparing the test pieces. In addition, for the sealing property, dye penetration was observed both after one day at 37° C. and after the TC 5000 test.

The amounts of the components and the test results of the dental curable composition are shown in Table 4.

Comparative Example 6

In Example 19, 5.0 parts by weight of diethanol p-toluidine (DEPT) and 0.5 part by weight of BPO were used without using NPG-Na and p-TSNa. As a result, the dental curable composition had a curing time of 4.3 minutes and a polymerization temperature of 43.4° C. The microtensile bond strength was unable to be tested because there occurred the peeling of the composition from the bond interface during the stage of preparing the test pieces. In addition, for the sealing property, dye penetration was observed both after one day at 37° C. and after the TC 5000 test.

The amounts of the components and the test results of the dental curable composition are shown in Table 4.

Comparative Example 7

In Example 23, 4.0 parts by weight of diethanol p-toluidine (DEPT) was used without using NPG-Na and p-TSNa. In addition, 0.5 part by weight of BPO was added. As a result, the dental curable composition had a curing time of 2.8 minutes and a polymerization temperature of 42.1° C. The microtensile bond strength was unable to be tested because the composition debonded from the test pieces during the storage under static conditions in a constant temperature bath at 37° C. for 24 hours. In addition, for the sealing property, dye penetration was observed both after one day at 37° C. and after the TC 5000 test.

The amounts of the components and the test results of the dental curable composition are shown in Table 4.

Comparative Example 8

In Example 24, 3.6 parts by weight of diethanol p-toluidine (DEPT) was used without using NPG-K. In addition, 3.0 parts by weight of BPO was added (the total amount was 103 parts by weight). As a result, the dental curable composition had a curing time of 1.8 minutes and a polymerization temperature of 42.9° C. The microtensile bond strength was unable to be tested because there occurred the peeling of the composition from the bond interface during the stage of preparing the test pieces. In addition, for the sealing property, dye penetration was observed both after one day at 37° C. and after the TC 5000 test.

The amounts of the components and the test results of the dental curable composition are shown in Table 4.

TABLE 3

| | Dental Curable Composition (parts by weight) | | | | | | | | |
|---|---|---|---|---|---|---|---|---|---|
| | ($A_0$) | ($B_0$) | | | | (C) or (CA) | (D) | (E) | (F) | |
| Ex. 18 | Phosphoric acid (0.5) | HEMA (47.0) | GDMA (22.2) | 2.6E (23.0) | | NPG-K (6.8) | P-TSNa (0.5) | — | — | |
| Ex. 19 | Citric acid (1.0) | HEMA (47.0) | GDMA (20.8) | 2.6E (13.8) | 3G (8.9) | NPG-Na (5.0) | P-TSNa (0.5) | $H_2O$ (3.0) | — | |
| Ex. 20 | Lactic acid (1.0) | HEMA (47.0) | A-9300 (21.3) | 2.6E (13.8) | 3G (8.1) | NPG-K (7.1) | P-TSNa (0.5) | $H_2O$ (1.2) | — | |
| Ex. 21 | Ascorbic acid (10.0) | HEMA (40.5) | A-9300 (15.0) | 2.6E (15.0) | 3G (4.0) | NPG (5.0) | P-TSNa (0.5) | $H_2O$ (10.0) | — | |
| Ex. 22 | Phosphoric acid (1.0) | HEMA (19.8) | A-9300 (12.2) | GDMA (10.5) | 3G (5.2) | NPG-Na (4.0) | P-TSNa (0.3) | — | $ZrO_2$ (40.8) | $SiO_2$ (6.5) |
| Ex. 23 | Citric acid (0.98) | HEMA (19.6) | A-9300 (12.4) | GDMA (10.5) | 3G (1.5) | NPG-Na (4.0) | P-TSNa (0.5) | $H_2O$ (3.5) | $ZrO_2$ (40.5) | $SiO_2$ (6.5) |
| Ex. 24 | Lactic acid (0.5) | HEMA (9.6) | A-9300 (12.4) | UDMA (19.6) | 3G (6.6) | NPG-K (3.6) | P-TSNa (0.3) | $H_2O$ (3.0) | $ZrO_2$ (39.4) | $SiO_2$ (5.0) |

TABLE 3-continued

| Ex. 25 | Ascorbic acid (0.1) | HEMA (13.5) | A-9300 (13.8) | GDMA (15.2) | 2.6E (3.3) | NPG* (8.6) | P-TSNa (1.0) | — | ZrO₂ (40.0) | SiO₂ (4.5) |
|---|---|---|---|---|---|---|---|---|---|---|

| | Dental Curable Composition (parts by weight) | | | | *4 | |
|---|---|---|---|---|---|---|
| | | | | | 30° C. | TC |
| | (G) | *1 | *2 | *3 | 1 day | 5000 |
| Ex. 18 | — | 68.0 | 37.6 | — | — | Do |
| Ex. 19 | — | 10.1 | 37.5 | 6.1 | Good | Good |
| Ex. 20 | — | 47.3 | 37.8 | 5.3 | Do | Do |
| Ex. 21 | — | 50.2 | 37.6 | 3.6 | Do | Do |
| Ex. 22 | — | 61.0 | 37.4 | 4.7 | Do | Do |
| Ex. 23 | CQ (0.01) DTMPO (0.01) | 9.0 | 37.5 | 7.7 | Very good | Good |
| Ex. 24 | — | 45.8 | 37.7 | 4.8 | Good | Good |
| Ex. 25 | — | 48.1 | 37.6 | — | Good | DO |

*1: Curing time (min)
*2: Polymerization temperature (° C.)
*3: Microtensile bond strength (MPa)
*4: Sealing property

TABLE 4

| | Comparative curable composition (parts by weight) | | Curing time (Min) | Polymerization temperature (° C.) | Microtensile bond strength (MPa) | Sealing Property | |
|---|---|---|---|---|---|---|---|
| | | | | | | 37° C. 1 day | TC5000 |
| Comparative Example 5 | Component A₀ | Phosphoric acid(0.5) | 2.3 | 43.7 | Test pieces could not be prepared | Very poor | Very poor |
| | Component B₀ | HEMA(47.0), GDMA(22.2), 2.6E(23.0) | | | | | |
| | Component C | DEPT(6.8) | | | | | |
| | Component D | — | | | | | |
| | Component E | — | | | | | |
| | Component F | — | | | | | |
| | Component G | — BPO(0.5) | | | | | |
| Comparative Example 6 | Component A₀ | Citric acid (1.0) | 4.3 | 43.4 | Test pieces could not be prepared | Poor | Very poor |
| | Component B₀ | HEMA(47.0), GDMA(20.8), 2.6E(13.8), 3G(8.9) | | | | | |
| | Component C | DEPT(5.0) | | | | | |
| | Component D | — | | | | | |
| | Component E | H2O(3.0) | | | | | |
| | Component F | — | | | | | |
| | Component G | — BPO(0.5) | | | | | |
| Comparative Example 7 | Component A₀ | Citric acid (0.98) | 2.8 | 42.1 | Debonded | Poor | Poor |
| | Component B₀ | HEMA(19.6), A-9300(12.4), GDMA(10.5), 3G(1.5) | | | | | |
| | Component C | DEPT(4.0) | | | | | |
| | Component D | — | | | | | |
| | Component E | H2O(3.5) | | | | | |
| | Component F | ZrO2(40.5), SiO2(6.5) | | | | | |
| | Component G | CQ(0.01), DTMPO(0.01) BPO(0.5) | | | | | |
| Comparative Example 8 | Component A₀ | Lactic acid (0.5) | 1.8 | 42.9 | Test pieces could not be prepared | Very poor | Very poor |
| | Component B₀ | HEMA(9.6), A-9300(12.4), UDMA(19.6), 3G(6.6) | | | | | |
| | Component C | DEPT(3.6) | | | | | |
| | Component D | P-TSNa(0.3) | | | | | |
| | Component E | H2O(3.0) | | | | | |
| | Component F | ZrO2(39.4), SiO2(5.0) | | | | | |
| | Component G | — BPO(3.0) | | | | | |

As shown in Table 3 and Table 4, the dental curable compositions of the present invention may be polymerized even when they do not contain peroxide as a polymerization initiator. Further, the compositions can be polymerized without inhibition by water even under wet conditions, and the heat of polymerization is nearly equal to the body temperature. The dental curable compositions have excellent adhesion to teeth without surface treatment, cause no gaps in the bonding interface and have excellent decomposition resistance. Therefore, they are not only extremely useful as a dental cement but also may greatly contribute to dental care.

Example 26

A dental curable composition of the present invention was prepared by adding 0.52 part by weight of NPG-Na into a solution in which 55.7 parts by weight of 4-MET, 39.8 parts by weight of HEMA and 3.98 parts by weight of distilled water were mixed in advance, and by mixing the resultant mixture on a mixing pad. The curing time and polymerization temperature after one minute from the start of the mixing were measured by DSC. The sealing test (at 37° C. for one day) was also carried out. The dental curable composition had a curing time of 42.6 minutes and a polymerization temperature of 37.2° C. The sealing property was good with the dye penetration being 0.5 or less.

Example 27

A dental curable composition of the present invention was prepared by mixing a liquid material including 9.5 parts by weight of 4-MET, 10.5 parts by weight of HEMA, 12.0 parts by weight of A-9300, 9.5 parts by weight of GDMA, 7.0 parts by weight of 2.6E, 1.5 parts by weight of distilled water, 0.001 part by weight of CQ and 0.001 part by weight of 2,4,6trimethylbenzoyldiphenylphosphine oxide (DTMPO), and a powder material including 3.5 parts by weight of NPG-Na, 0.3 part by weight of p-TSNa, 40.0 parts by weight of zirconium oxide with an average particle size of 2 μm and 6.198 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 7.2 minutes, a polymerization temperature of 37.5° C. and a microtensile bond strength of 17.8 MPa. The sealing property was excellent, that is, no dye penetration was observed both after one day at 37° C. and even after the TC 5000 test.

Example 28

A dental curable composition of the present invention was prepared by mixing a liquid material including 17.6 parts by weight of 4-MET, 8.4 parts by weight of HEMA, 9.6 parts by weight of A-9300, 7.6 parts by weight of GDMA, 5.6 parts by weight of 2.6E, 1.2 parts by weight of distilled water, 0.001 part by weight of CQ and 0.001 part by weight of 2,4,6trimethylbenzoyldiphenylphosphine oxide (DTMPO), and a powder material including 3.5 parts by weight of NPG-Na, 40.3 parts by weight of zirconium oxide with an average particle size of 2 μm and 6.198 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 5.6 minutes, a polymerization temperature of 37.5° C. and a microtensile bond strength of 16.6 MPa. The sealing property was excellent, that is, no dye penetration was observed both after one day at 37° C. and even after the TC 5000 test.

Example 29

A dental curable composition of the present invention was prepared by mixing a liquid material including 17.6 parts by weight of 4-MET, 8.4 parts by weight of HEMA, 9.6 parts by weight of A-9300, 7.6 parts by weight of GDMA, 5.6 parts by weight of 2.6E, 1.2 parts by weight of distilled water, 0.001 part by weight of CQ and 0.001 part by weight of 2,4,6-trimethylbenzoyldiphenylphosphine oxide (DTMPO), and a powder material including 3.5 parts by weight of NPG-Na, 0.3 part by weight of p-TSNa, 40.0 parts by weight of zirconium oxide with an average particle size of 2 μm and 6.198 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 5.8 minutes, a polymerization temperature of 37.4° C. and a microtensile bond strength of 17.2 MPa. The sealing property was excellent, that is, no dye penetration was observed both after one day at 37° C. and even after the TC 5000 test.

Example 30

A dental curable composition of the present invention was prepared by mixing a liquid material including 23.3 parts by weight of 4-MET, 10.3 parts by weight of HEMA, 6.6 parts by weight of 3G, 3.8 parts by weight of VR90, 5.2 parts by weight of GDMA, 0.8 part by weight of distilled water, 0.001 part by weight of CQ and 0.001 part by weight of 2,4,6-trimethylbenzoyldiphenylphosphine oxide (DTMPO), and a powder material including 3.5 parts by weight of NPG-Na, 0.3 part by weight of p-TSNa, 40.0 parts by weight of zirconium oxide with an average particle size of 2 μm and 6.198 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 5.0 minutes, a polymerization temperature of 37.4° C. and a microtensile bond strength of 11.2 MPa. The sealing property was excellent, that is, no dye penetration was observed both after one day at 37° C. and even after the TC 5000 test.

Example 31

A dental curable composition of the present invention was prepared by mixing a liquid material including 9.5 parts by weight of 4-MET, 10.5 parts by weight of HEMA, 12.0 parts by weight of A-9300, 7.0 parts by weight of 2.6E, 9.5 parts by weight of GDMA, 1.5 parts by weight of distilled water, 0.0005 part by weight of CQ and 0.0005 part by weight of 2,4,6-trimethylbenzoyldiphenylphosphine oxide (DTMPO), and a powder material including 3.5 parts by weight of NPG-Na, 0.3 part by weight of p-TSNa, 40.0 parts by weight of zirconium oxide with an average particle size of 2 μm and 6.199 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 7.2 minutes, a polymerization temperature of 37.3° C. and a microtensile bond strength of 16.7 MPa. The sealing property was excellent, that is, no dye penetration was observed both after one day at 37° C. and even after the TC 5000 test.

Example 32

A dental curable composition of the present invention was prepared by mixing a liquid material including 6.3 parts by weight of 4-MET, 7.0 parts by weight of HEMA, 8.0 parts by weight of A-9300, 4.67 parts by weight of 2.6E, 6.33 parts by weight of GDMA, 1.0 part by weight of distilled water, 0.0005 part by weight of CQ and 0.0005 part by weight of 2,4,6-trimethylbenzoyldiphenylphosphine oxide (DTMPO), and a powder material including 4.7 parts by weight of NPG-Na, 0.4 part by weight of p-TSNa, 53.3 parts by weight of zirconium oxide with an average particle size of 2 μm and 8.299 parts by weight of spherical silica with an average particle size of 5 μm, on a mixing pad. The curing time and polymerization temperature after one minute from the start of the mixing were measured by DSC. The microtensile bond strength test and the sealing test were also carried out. As a result, the dental curable composition had a curing time of 5.8 minutes, a polymerization temperature of 37.8° C. and a microtensile bond strength of 18.9 MPa. The sealing property was excellent, that is, no dye penetration was observed both after one day at 37° C. and even after the TC 5000 test.

The amounts of the components and the test results of the dental curable composition are shown in Table 5.

face treatment, cause no gaps in the bonding interface and have excellent decomposition resistance. Therefore, they are not only extremely useful as a dental cement but also may greatly contribute to dental care.

Example 33

A dental curable composition of the present invention was prepared by mixing 33 parts by weight of 4-MET, 66 parts by weight of 3G and 1 part by weight of NPG on a mixing pad. The mixture was sufficiently mixed, and a given amount of the resultant dental curable composition was allowed to stand on a detector of FI-IR instrument and then the measurements were carried out. First, the peak height ratio (C═C/C═O) was determined with the composition before the composition was irradiated with light. The peak height ratio (C═C/C═O) was then determined with the composition after the composition was irradiated with light for three minutes. By the above-described calculation method, the photo-polymerization degree was found to be 34%.

TABLE 5

| | Dental Curable Composition (parts by weight) | | | | | | | | |
|---|---|---|---|---|---|---|---|---|---|
| | (AB) | | ($B_0$) | | | (C) or (CA) | (D) | (E) | (F) | |
| Ex. 26 | 4-MET (55.7) | HEMA (39.8) | | | | NPG-Na (0.52) | — | $H_2O$ (3.98) | — | |
| Ex. 27 | 4-MET (9.5) | HEMA (10.5) | A-9300 (12.0) | 2.6E (7.0) | GDMA (9.5) | NPG-Na (3.5) | P-TSNa (0.3) | $H_2O$ (1.5) | $ZrO_2$ (40) | $SiO_2$ (6.198) |
| Ex. 28 | 4-MET (17.6) | HEMA (8.4) | A-9300 (9.6) | 2.6E (5.6) | GDMA (7.6) | NPG-Na (3.5) | — | $H_2O$ (1.2) | $ZrO_2$ (40.3) | $SiO_2$ (6.198) |
| Ex. 29 | 4-MET (17.6) | HEMA (8.4) | A-9300 (9.6) | 2.6E (5.6) | GDMA (7.6) | NPG-Na (3.5) | P-TSNa (0.3) | $H_2O$ (1.2) | $ZrO_2$ (40) | $SiO_2$ (6.198) |
| Ex. 30 | 4-MET (23.3) | HEMA (10.3) | 3G (6.6) | VR90 (3.8) | GDMA (5.2) | NPG-Na (3.5) | P-TSNa (0.3) | $H_2O$ (0.8) | $ZrO_2$ (40) | $SiO_2$ (6.198) |
| Ex. 31 | 4-MET (9.5) | HEMA (10.5) | A-9300 (12.0) | 2.6E (7.0) | GDMA (9.5) | NPG-Na (3.5) | P-TSNa (0.3) | $H_2O$ (1.5) | $ZrO_2$ (40) | $SiO_2$ (6.199) |
| Ex. 32 | 4-MET (6.3) | HEMA (7.0) | A-9300 (8.0) | 2.6E (4.67) | GDMA (6.33) | NPG-Na (4.7) | P-TSNa (0.4) | $H_2O$ (1.0) | $ZrO_2$ (53.3) | $SiO_2$ (8.299) |

| | Dental Curable Composition (parts by weight) | | | | | *4 | |
|---|---|---|---|---|---|---|---|
| | (G) | | *1 | *2 | *3 | 30° C. 1 day | TC 5000 |
| Ex. 26 | — | | 42.6 | 37.2 | — | Do | — |
| Ex. 27 | CQ (0.001) | DTMPO (0.001) | 7.2 | 37.5 | 17.8 | Very good | Very good |
| Ex. 28 | CQ (0.001) | DTMPO (0.001) | 5.6 | 37.5 | 16.6 | Very good | Very good |
| Ex. 29 | CQ (0.001) | DTMPO (0.001) | 5.8 | 37.4 | 17.2 | Very good | Very good |
| Ex. 30 | CQ (0.001) | DTMPO (0.001) | 5 | 37.4 | 11.2 | Very good | Very good |
| Ex. 31 | CQ (0.0005) | DTMPO (0.0005) | 7.2 | 37.3 | 16.7 | Very good | Very good |
| Ex. 32 | CQ (0.0005) | DTMPO (0.0005) | 5.8 | 37.8 | 18.9 | Very good | Very good |

*1: Curing time (min)
*2: Polymerization temperature (° C.)
*3: Microtensile bond strength (MPa)
*4: Sealing property As shown in Table 5, the dental curable compositions of the present invention may be polymerized even when they do not contain peroxide as a polymerization initiator. Further, the compositions can be polymerized without inhibition by water even under wet conditions, and the heat of polymerization is nearly equal to the body temperature. The dental curable compositions have excellent adhesion to teeth without sur-

Example 34

A dental curable composition of the present invention was prepared by mixing 33 parts by weight of 4-MET, 66 parts by weight of 3G and 1 part by weight of NPG-Na on a mixing pad. The mixture was sufficiently mixed, and a given amount of the resultant dental curable composition was allowed to stand on a detector of FI-IR instrument and then the measurements were carried out. First, the peak height ratio (C=C/C=O) was determined with the composition before the composition was irradiated with light. The peak height ratio (C=C/C=O) was then determined with the composition after the composition was irradiated with light for three minutes. By the above calculation method, the photo-polymerization degree was found to be 33%.

Example 35

A dental curable composition of the present invention was prepared by mixing 33 parts by weight of 4-MET, 65.5 parts by weight of 3G, 1 part by weight of NPG-Na and 0.5 part by weight of p-TSNa on a mixing pad. The mixture was sufficiently mixed, and a given amount of the resultant dental curable composition was allowed to stand on a detector of FI-IR instrument and then the measurements were carried out. First, the peak height ratio (C=C/C=O) was determined with the composition before the composition was irradiated with light. The peak height ratio (C=C/C=O) was then determined with the composition after the composition was irradiated with light for three minutes. By the above calculation method, the photo-polymerization degree was found to be 32%.

Comparative Example 9

In Example 33, the similar test was carried out by using DEPT without using NPG. As a result, the height of the peaks (C=C and C=O) did not change before and after the light irradiation, and the photo-polymerization degree was found to be 0%.

The test results are shown in Table 6.

TABLE 6

| | Dental Composition (parts by weight) | | | | Polymerization Degree (%) |
|---|---|---|---|---|---|
| | (AB) | (B0) | (C) or (CA) | (D) | |
| Ex. 33 | 4-MET (33) | 3G (66) | NPG (1) | — | 34 |
| Ex. 34 | 4-MET (33) | 3G (66) | NPG-Na (1) | — | 33 |
| Ex. 35 | 4-META (33) | HEMA (65.5) | NPG (1) | p-TSNa (0.5) | 32 |
| Comp. Ex. 9 | 4-META (33) | HEMA (66) | DEPT (1) | — | 0 |

As is clear from Table 6, the dental curable compositions of the present invention may be polymerized using NPG, NPG-Na or the like without using other polymerization initiators.

The dental curable composition of the present invention may be polymerized without using a peroxide-based polymerization initiator as mentioned above and the curing time (polymerization time=usable time) is within a range in which the composition can be suitably used as a dental curing agent. Further, the polymerization temperature is nearly equal to the body temperature and is not high compared with the body temperature of a patient. Therefore, the patient does not feel uncomfortable when the dental curable composition of the present invention is applied to the patient.

Furthermore, the dental curable composition of the present invention has excellent adhesion and sealing property with the tooth surface that is not pretreated. Therefore, it is very unlikely that a new disease is induced from the bonded portion. Thus, the composition enables safe dental care.

The invention claimed is:

1. A dental curable composition that has a curing time of 30 seconds to 120 minutes and comprises the following components:
   (A) a compound having an acidic group in the molecule,
   (B) a polymerizable monomer,
   (C) an organic amine compound,
   (D) a sulfur-containing reducing compound, and
   (G) a photo-polymerization initiator;
   the composition containing:
   the component (A) in an amount of 0.01 to 80 parts by weight,
   the component (B) in an amount of 21 to 99.8 parts by weight,
   the component (C) in an amount of 0.01 to 30 parts by weight, and
   the component (D) in an amount of 0 to 30 parts by weight;
   wherein the total of the components (A) to (D) is 100 parts by weight; and when any compound belongs to a plurality of the components (A) to (D), the parts by weight of the compound is divided by the number of the components to which the compound belongs, and the quotient is used as the content of each component,
   wherein the component (C) is an aromatic amine, and
   wherein the ratio of the component (G) to the component (C) (G/C) is from 0.000033 to less than 0.0005.

2. The dental curable composition according to claim 1, wherein the compounds having an acidic group in the molecule (A) include a nonpolymerizable monomer having an acidic group in the molecule ($A_0$) and the content of the component ($A_0$) is 0.01 to 30 parts by weight.

3. The dental curable composition according to claim 1, wherein the polymerizable monomers (B) include a polymerizable monomer having no acidic group in the molecule ($B_0$) and the content of the component ($B_0$) is 21 to 99.8 parts by weight.

4. The dental curable composition according to claim 1, wherein the composition contains a polymerizable monomer having an acidic group in the molecule (AB) as the compound having an acidic group in the molecule (A) and the polymerizable monomer (B) and the content of the polymerizable monomer (AB) is 1 to 50 parts by weight.

5. The dental curable composition according to claim 4, wherein the polymerizable monomer having an acidic group in the molecule (AB) is a compound having at least one acidic group in the molecule selected from the group consisting of a carboxylic acid group, a phosphoric acid group, a thiophosphoric acid group, a sulfonic acid group, a pyrophosphoric acid group and a sulfinic acid group.

6. The dental curable composition according to claim 1, wherein the polymerizable monomer (B) is a polymerizable monomer having at least one hydroxyl group in the molecule.

7. The dental curable composition according to claim 1, wherein the polymerizable monomer (B) is a polymerizable monomer having a triazine ring.

8. The dental curable composition according to claim 1, wherein the organic amine compound component (C) is a photo-polymerization initiator represented by the following formula (I):

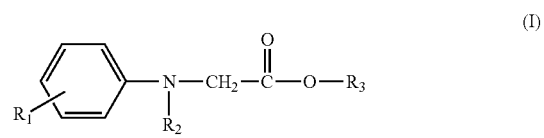

wherein $R_1$ and $R_2$ are each independently a hydrogen atom, or an alkyl group optionally having a functional group or a substituent, and $R_3$ is a hydrogen atom or a metal atom.

9. The dental curable composition according to claim 1, wherein the organic amine compound component (C) is an amine compound represented by the following formula (I) or an amine compound represented by the following formula (II):

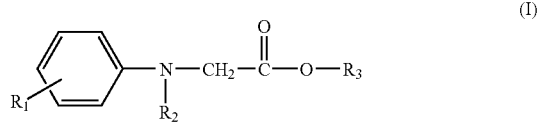

(I)

wherein $R_1$ and $R_2$ are each independently a hydrogen atom, or an alkyl group optionally having a functional group or a substituent, and $R_3$ is a hydrogen atom or a metal atom;

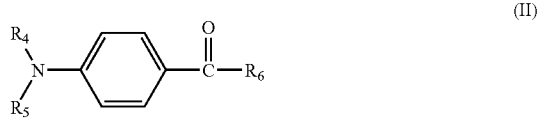

(II)

wherein $R_4$ and $R_5$ are each independently a hydrogen atom or an alkyl group; and $R_6$ is a hydrogen atom, or an alkyl group or an alkoxyl group optionally having a functional group or a substituent.

10. The dental curable composition according to claim 1, wherein the sulfur-containing reducing compound (D) is an organic sulfur-containing compound selected from the group consisting of an organic sulfinic acid, an organic sulfinic acid salt, an organic sulfonic acid and an organic sulfonic acid salt, and/or an inorganic sulfur-containing compound.

11. The dental curable composition according to claim 1, wherein the dental curable composition further comprises an aqueous solvent component (E).

12. The dental curable composition according to claim 11, wherein the content of the component (E) is 0.1 to 70 parts by weight and wherein the total amount of the composition is 100 parts by weight.

13. The dental curable composition according to claim 11, wherein the content of the component (E) is 0.1 to 9.9 parts by weight and wherein the total amount of the composition is 100 parts by weight.

14. The dental curable composition according to claim 1, wherein the dental curable composition further comprises at least one filing material component (F) selected from an inorganic filing material, an organic filing material and an organic composite filing material.

15. The dental curable composition according to claim 14, wherein the content of the component (F) is 5 to 70 parts by weight and wherein the total amount of the composition is 100 parts by weight.

16. The dental curable composition according to claim 14, wherein the content of the component (F) is 11 to 70 parts by weight and wherein the total amount of the composition is 100 parts by weight.

17. The dental curable composition according to claim 1, wherein the content of the component (G) is 0.0001 to 5 parts by weight and wherein the total amount of the composition is 100 parts by weight.

18. The dental curable composition according to claim 1, wherein the dental curable composition is polymerized and cured with visible light.

19. The dental curable composition according to claim 1, wherein the polymerization temperature when the composition is polymerized is not more than 60° C.

20. A sealer cement for root canal obturation comprising the dental curable composition of claim 1.

* * * * *

UNITED STATES PATENT AND TRADEMARK OFFICE
CERTIFICATE OF CORRECTION

PATENT NO.       : 8,362,105 B2                                          Page 1 of 1
APPLICATION NO.  : 12/063200
DATED            : January 29, 2013
INVENTOR(S)      : Ori et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this
First Day of September, 2015

Michelle K. Lee
*Director of the United States Patent and Trademark Office*